(12) United States Patent
Steinbach

(10) Patent No.: US 8,211,060 B2
(45) Date of Patent: Jul. 3, 2012

(54) REDUCED SIZE IMPLANTABLE PUMP

(75) Inventor: Bernd Steinbach, Friedberg (DE)

(73) Assignee: Palyon Medical (BVI) Limited, Tortola (VG)

( * ) Notice: Subject to any disclaimer, the term of this patent is extended or adjusted under 35 U.S.C. 154(b) by 696 days.

(21) Appl. No.: 11/126,101

(22) Filed: May 10, 2005

(65) Prior Publication Data

US 2006/0259016 A1 Nov. 16, 2006

(51) Int. Cl.
*A61M 37/00* (2006.01)

(52) U.S. Cl. ........ 604/141; 604/153; 604/247; 604/249; 604/891.1

(58) Field of Classification Search .......... 604/131–133, 604/140–141, 145–146, 153, 247, 249, 891, 604/1, 890.1, 891.1; 128/DIG. 12
See application file for complete search history.

(56) References Cited

U.S. PATENT DOCUMENTS

| | | | |
|---|---|---|---|
| 3,951,147 A * | 4/1976 | Tucker et al. | ............... 604/891.1 |
| 4,077,405 A | 3/1978 | Haerten et al. | |
| 4,187,870 A | 2/1980 | Akkerman | |
| 4,193,397 A | 3/1980 | Tucker et al. | |
| 4,270,532 A | 6/1981 | Franetzki et al. | |
| 4,299,220 A | 11/1981 | Dorman | |
| 4,373,527 A | 2/1983 | Fischell | |
| 4,411,651 A | 10/1983 | Schulman | |
| 4,443,218 A | 4/1984 | DeCant, Jr. et al. | |
| 4,447,224 A | 5/1984 | DeCant, Jr. et al. | |
| 4,486,190 A | 12/1984 | Reinicke | |
| 4,496,343 A | 1/1985 | Prosl et al. | |
| 4,511,163 A | 4/1985 | Harris et al. | |
| 4,557,726 A | 12/1985 | Reinicke | |
| 4,573,994 A | 3/1986 | Fischell et al. | |
| 4,626,244 A | 12/1986 | Reinicke | |
| 4,627,840 A | 12/1986 | Cuadra et al. | |
| 4,639,244 A | 1/1987 | Rizk et al. | |
| 4,661,097 A | 4/1987 | Fischell et al. | |
| 4,671,320 A | 6/1987 | Grifols Lucas | |
| 4,685,902 A * | 8/1987 | Edwards et al. | ............... 604/153 |
| 4,714,462 A | 12/1987 | DiDomenico | |
| 4,718,893 A | 1/1988 | Dorman et al. | |
| 4,738,665 A | 4/1988 | Shepard | |
| 4,772,263 A * | 9/1988 | Dorman et al. | ............... 604/132 |
| 4,772,270 A | 9/1988 | Wiita et al. | |

(Continued)

FOREIGN PATENT DOCUMENTS

DE 9107030 6/1991

(Continued)

OTHER PUBLICATIONS

International Search Report, PCT/US06/18981, Jan. 16, 2007.

(Continued)

*Primary Examiner* — Kevin C Sirmons
*Assistant Examiner* — Emily Schmidt
(74) *Attorney, Agent, or Firm* — Lerner, David, Littenberg, Krumholz & Mentlik, LLP

(57) ABSTRACT

A variable hydraulic resistor for use with implantable pumps is disclosed. The variable hydraulic resistor according to the present invention is particularly useful in varying the flow rate of a medication fluid from an otherwise constant flow implantable pump. An implantable pump is also disclosed, which does not require a complicated clinching system or the like, and which may include an undulating membrane and chamber design to reduce the height of the pump.

47 Claims, 19 Drawing Sheets

U.S. PATENT DOCUMENTS

| | | | |
|---|---|---|---|
| 4,838,887 A | 6/1989 | Idriss | |
| 4,915,690 A | 4/1990 | Cone et al. | |
| 4,931,050 A * | 6/1990 | Idriss | 604/891.1 |
| 4,955,861 A | 9/1990 | Enegren et al. | |
| 4,969,873 A | 11/1990 | Steinbach et al. | |
| 4,978,338 A | 12/1990 | Melsky et al. | |
| 5,015,374 A | 5/1991 | Mathieu et al. | |
| 5,045,060 A | 9/1991 | Melsky et al. | |
| 5,061,242 A | 10/1991 | Sampson | |
| 5,067,943 A | 11/1991 | Burke | |
| 5,085,656 A | 2/1992 | Polaschegg | |
| 5,088,983 A | 2/1992 | Burke | |
| 5,135,498 A | 8/1992 | Kam et al. | |
| 5,146,933 A | 9/1992 | Boyd | |
| 5,147,483 A | 9/1992 | Melsky et al. | |
| 5,163,920 A | 11/1992 | Olive | |
| 5,205,819 A | 4/1993 | Ross et al. | |
| 5,207,666 A | 5/1993 | Idriss et al. | |
| 5,217,442 A | 6/1993 | Davis | |
| 5,242,406 A * | 9/1993 | Gross et al. | 604/132 |
| 5,336,194 A | 8/1994 | Polaschegg et al. | |
| 5,395,324 A | 3/1995 | Hinrichs et al. | |
| 5,405,339 A | 4/1995 | Kohnen et al. | |
| 5,445,616 A | 8/1995 | Kratoska et al. | |
| 5,462,525 A | 10/1995 | Srisathapat et al. | |
| 5,474,552 A | 12/1995 | Palti | |
| 5,549,866 A | 8/1996 | Grifols Lucas | |
| 5,569,186 A | 10/1996 | Lord et al. | |
| 5,575,770 A | 11/1996 | Melsky et al. | |
| 5,637,102 A | 6/1997 | Tolkoff et al. | |
| 5,665,070 A | 9/1997 | McPhee | |
| 5,667,504 A | 9/1997 | Baumann et al. | |
| 5,704,915 A | 1/1998 | Melsky et al. | |
| 5,722,957 A | 3/1998 | Steinbach | |
| 5,766,150 A | 6/1998 | Langkau | |
| 5,769,823 A | 6/1998 | Otto et al. | |
| 5,785,681 A | 7/1998 | Indravudh | |
| 5,785,688 A | 7/1998 | Joshi et al. | |
| 5,792,104 A | 8/1998 | Speckman et al. | |
| 5,814,019 A * | 9/1998 | Steinbach et al. | 604/131 |
| 5,836,915 A | 11/1998 | Steinbach et al. | |
| 5,840,063 A | 11/1998 | Flaherty | |
| 5,904,666 A | 5/1999 | DeDecker et al. | |
| 5,931,829 A | 8/1999 | Burbank et al. | |
| 5,949,632 A | 9/1999 | Barreras, Sr. et al. | |
| 5,957,891 A | 9/1999 | Kriesel et al. | |
| 5,980,508 A * | 11/1999 | Cardamone et al. | 604/890.1 |
| 6,048,328 A | 4/2000 | Haller et al. | |
| 6,166,518 A | 12/2000 | Echarri et al. | |
| 6,181,105 B1 | 1/2001 | Cutolo et al. | |
| 6,203,523 B1 | 3/2001 | Haller et al. | |
| 6,213,972 B1 | 4/2001 | Butterfield et al. | |
| 6,238,369 B1 | 5/2001 | Burbank et al. | |
| 6,278,258 B1 | 8/2001 | Echarri et al. | |
| 6,280,416 B1 * | 8/2001 | Van Antwerp et al. | 604/141 |
| 6,283,944 B1 | 9/2001 | McMullen et al. | |
| 6,349,740 B1 | 2/2002 | Cho et al. | |
| 6,416,291 B1 | 7/2002 | Butterfield et al. | |
| 6,416,495 B1 | 7/2002 | Kriesel et al. | |
| 6,423,029 B1 | 7/2002 | Elsberry | |
| 6,464,671 B1 | 10/2002 | Elver et al. | |
| 6,471,645 B1 | 10/2002 | Warkentin | |
| 6,471,675 B1 | 10/2002 | Rogers et al. | |
| 6,488,652 B1 | 12/2002 | Weijand et al. | |
| 6,558,320 B1 | 5/2003 | Causey, III et al. | |
| 6,562,001 B2 | 5/2003 | Lebel et al. | |
| 6,577,899 B2 | 6/2003 | Lebel et al. | |
| 6,589,205 B1 | 7/2003 | Meadows | |
| 6,620,151 B2 | 9/2003 | Blischak et al. | |
| 6,638,263 B1 | 10/2003 | Theeuwes et al. | |
| 6,641,533 B2 | 11/2003 | Causey, III et al. | |
| 6,648,821 B2 | 11/2003 | Lebel et al. | |
| 6,652,510 B2 | 11/2003 | Lord et al. | |
| 6,664,763 B2 | 12/2003 | Echarri et al. | |
| 6,673,091 B1 | 1/2004 | Shaffer et al. | |
| 6,676,104 B2 | 1/2004 | Tillander | |
| 6,687,546 B2 | 2/2004 | Lebel et al. | |
| 6,702,779 B2 | 3/2004 | Connelly et al. | |
| 6,719,739 B2 | 4/2004 | Verbeek et al. | |
| 6,749,587 B2 | 6/2004 | Flaherty | |
| 6,764,472 B1 | 7/2004 | Burke et al. | |
| 6,805,687 B2 | 10/2004 | Dextradeur et al. | |
| 6,814,547 B2 | 11/2004 | Childers et al. | |
| 6,869,275 B2 | 3/2005 | Dante et al. | |
| 6,878,135 B1 | 4/2005 | Haller et al. | |
| 6,895,419 B1 | 5/2005 | Cargin, Jr. et al. | |
| 6,902,544 B2 | 6/2005 | Ludin et al. | |
| 6,932,114 B2 | 8/2005 | Sparks | |
| 6,997,919 B2 | 2/2006 | Olsen et al. | |
| 7,018,384 B2 | 3/2006 | Skakoon | |
| 7,083,593 B2 | 8/2006 | Stultz | |
| 7,108,686 B2 | 9/2006 | Burke et al. | |
| 7,150,741 B2 | 12/2006 | Erickson et al. | |
| 7,214,221 B2 | 5/2007 | Fentress et al. | |
| 7,367,968 B2 | 5/2008 | Rosenberg et al. | |
| 2002/0022759 A1 | 2/2002 | Forsell | |
| 2002/0072721 A1 | 6/2002 | Verbeek et al. | |
| 2002/0120186 A1 | 8/2002 | Keimel | |
| 2002/0156463 A1 | 10/2002 | Berrigan | |
| 2002/0193751 A1 | 12/2002 | Theeuwes et al. | |
| 2003/0208184 A1 * | 11/2003 | Burke et al. | 604/891.1 |
| 2003/0214199 A1 | 11/2003 | Heim et al. | |
| 2003/0216683 A1 | 11/2003 | Shekalim | |
| 2004/0005433 A1 | 1/2004 | Iguchi et al. | |
| 2004/0005931 A1 | 1/2004 | Wang et al. | |
| 2004/0054333 A1 | 3/2004 | Theeuwes et al. | |
| 2004/0055648 A1 | 3/2004 | Erickson | |
| 2004/0059315 A1 | 3/2004 | Erickson et al. | |
| 2004/0068224 A1 | 4/2004 | Couvillon et al. | |
| 2004/0143242 A1 | 7/2004 | Ludin et al. | |
| 2004/0153029 A1 | 8/2004 | Blischak et al. | |
| 2004/0202691 A1 | 10/2004 | Richard | |
| 2004/0204673 A1 | 10/2004 | Flaherty | |
| 2004/0254565 A1 | 12/2004 | Russell | |
| 2005/0011374 A1 | 1/2005 | Dejakum et al. | |
| 2005/0024175 A1 | 2/2005 | Gray et al. | |
| 2005/0037078 A1 | 2/2005 | Kuo et al. | |
| 2005/0038396 A1 | 2/2005 | Claude et al. | |
| 2005/0054988 A1 | 3/2005 | Rosenberg et al. | |
| 2005/0065500 A1 | 3/2005 | Couvillon et al. | |
| 2005/0070883 A1 | 3/2005 | Brown et al. | |
| 2005/0075624 A1 | 4/2005 | Miesel | |
| 2005/0101942 A1 | 5/2005 | Gillis et al. | |
| 2005/0113745 A1 | 5/2005 | Stultz | |
| 2005/0113892 A1 | 5/2005 | Sproul | |
| 2005/0187515 A1 | 8/2005 | Varrichio et al. | |
| 2005/0197652 A1 | 9/2005 | Nat | |
| 2005/0273081 A1 | 12/2005 | Olsen | |
| 2005/0273082 A1 | 12/2005 | Olsen | |
| 2005/0273083 A1 | 12/2005 | Lebel et al. | |
| 2006/0089619 A1 | 4/2006 | Ginggen | |
| 2006/0253135 A1 | 11/2006 | Ortiz | |
| 2006/0259015 A1 | 11/2006 | Steinbach | |
| 2006/0259016 A1 | 11/2006 | Steinbach | |
| 2006/0271021 A1 | 11/2006 | Steinbach | |
| 2006/0271022 A1 | 11/2006 | Steinbach et al. | |
| 2007/0005044 A1 | 1/2007 | Steinbach et al. | |
| 2007/0112328 A1 | 5/2007 | Steinbach et al. | |

FOREIGN PATENT DOCUMENTS

| | | |
|---|---|---|
| EP | 0 045 668 | * 10/1982 |
| FR | 2628639 | 9/1989 |
| JP | 2002-292683 | 10/2002 |
| WO | 03/068049 | 8/2003 |
| WO | 2005007223 | 1/2005 |
| WO | 2005044343 | 5/2005 |
| WO | 2005079885 | 9/2005 |
| WO | 2006/122330 | 11/2006 |

OTHER PUBLICATIONS

International Search Report, PCT/US2007/024026, Jul. 21, 2008.
Elliptec Resonant Actuator, X15G Preliminary Datasheet, Oct. 2004.
Website printout: www.medtronic.com/neuro/paintherapies/pain; N'Vision Programmer Discussion.

* cited by examiner

FIG. 10A
FIG. 10B
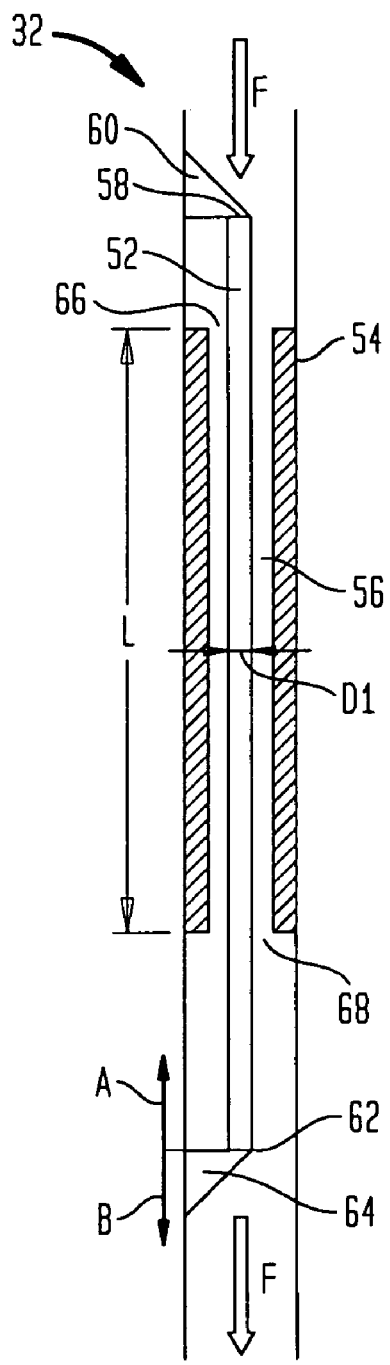
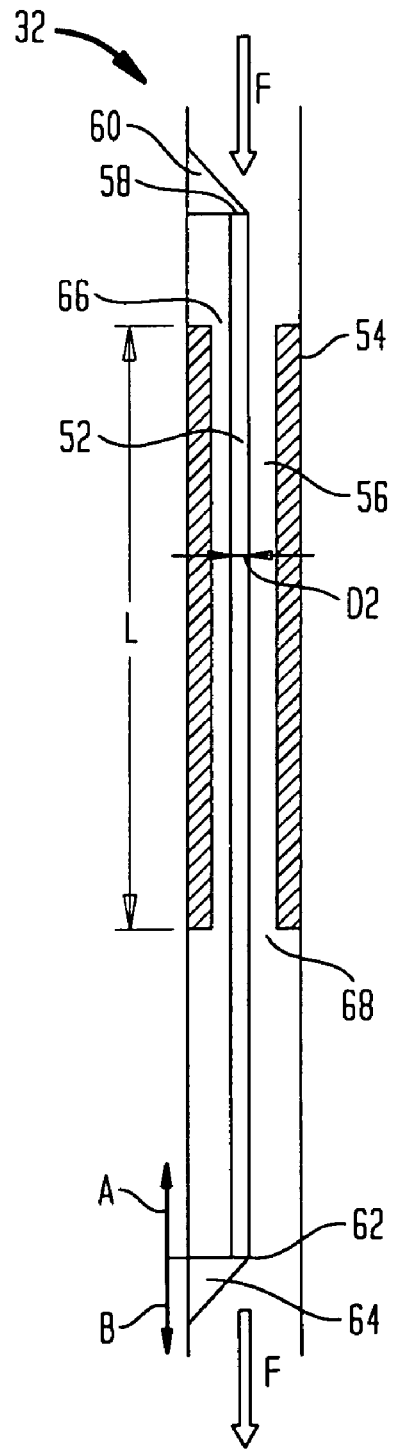

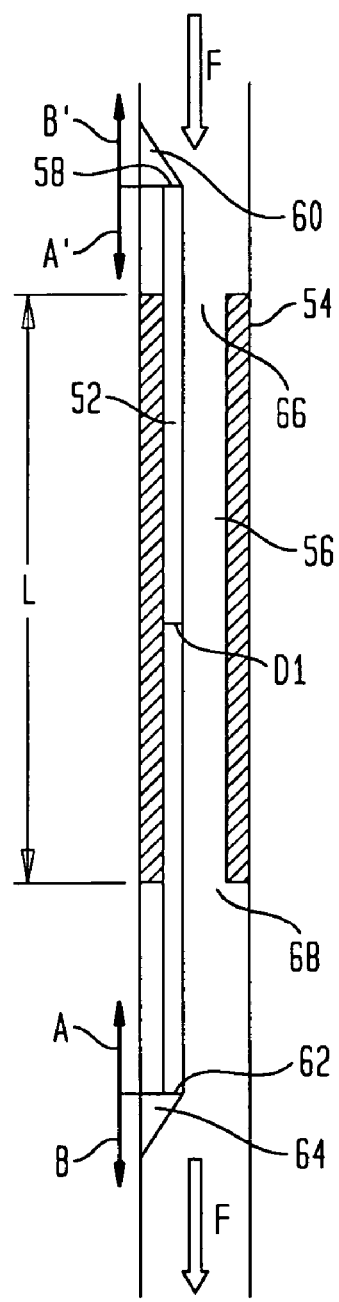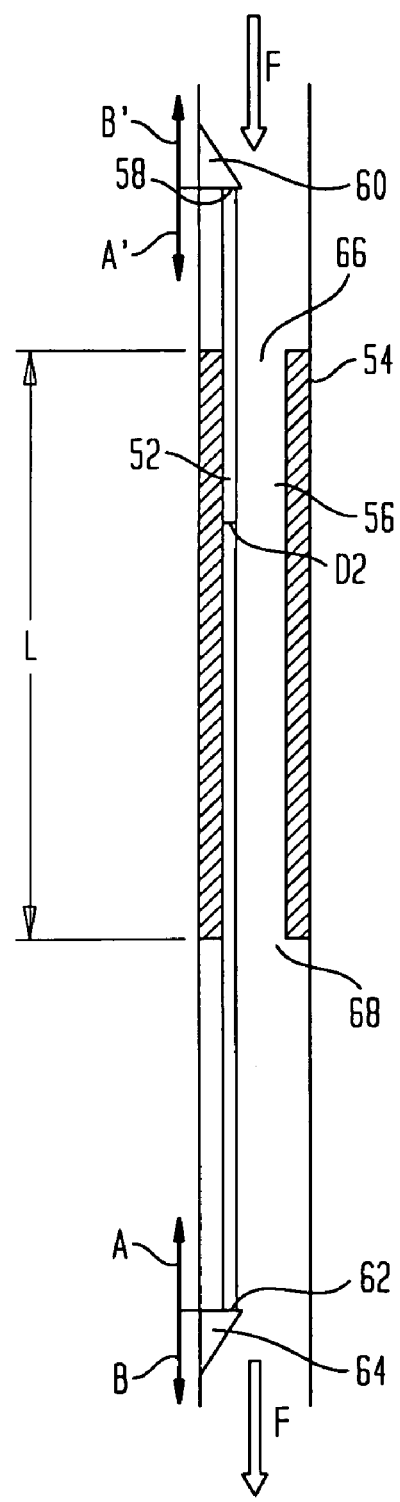

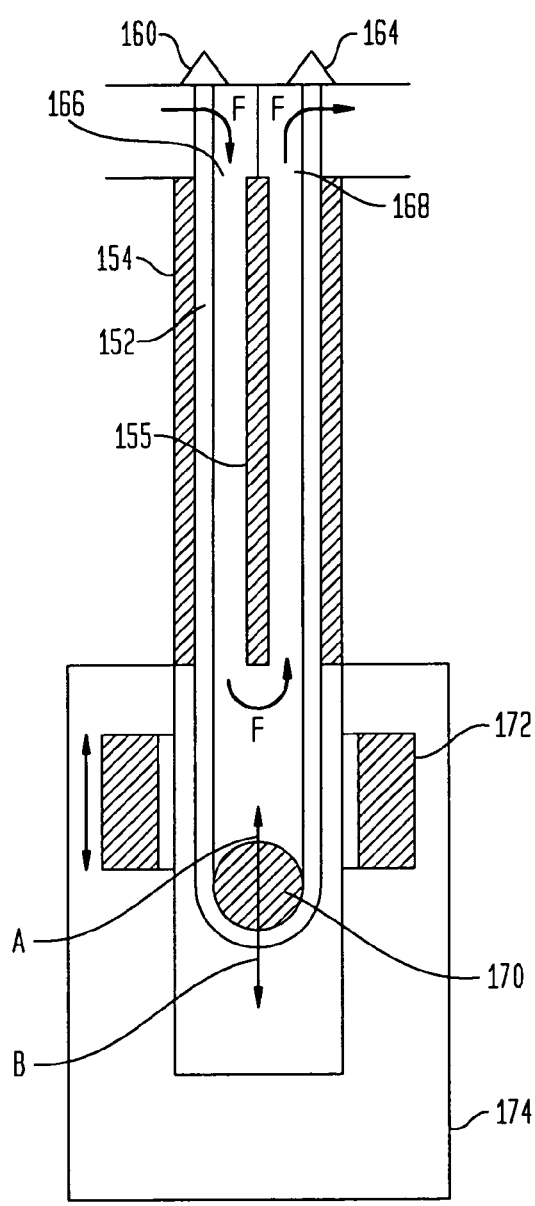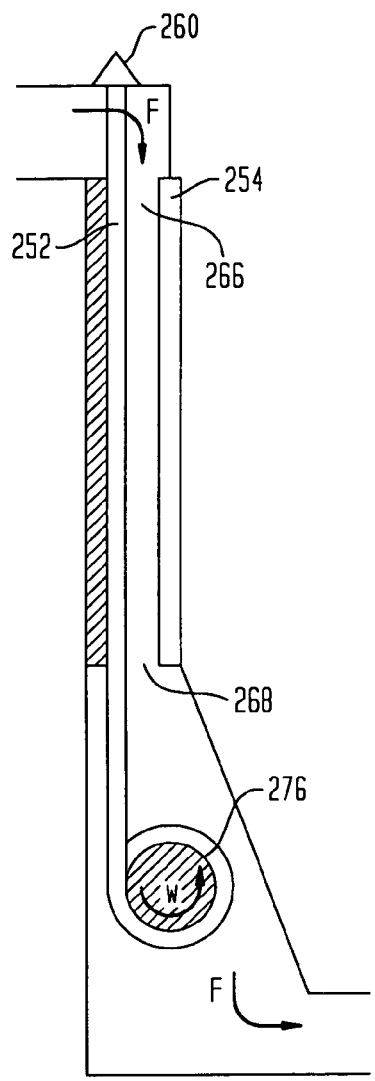

REDUCED SIZE IMPLANTABLE PUMP

BACKGROUND OF THE INVENTION

The present invention relates to implantable devices, and more particularly to a reduced size implantable pump and a programmable implantable pump allowing for variable flow rates in delivering medication or other fluid to a selected site in the human body.

Implantable pumps have been well known and widely utilized for many years. Typically, pumps of this type are implanted into patients who require the delivery of active substances or medication fluids to specific areas of their body. For example, patients that are experiencing severe pain may require painkillers daily or multiple times per day. Absent the use of an implantable pump or the like, a patient of this type would be subjected to one or more painful injections of such medication fluids. In the case of pain associated with more remote areas of the body, such as the spine, these injections may be extremely difficult to administer and particularly painful for the patient. Furthermore, attempting to treat conditions such as this through oral or intravascular administration of medication often requires higher doses of medication and may cause severe side effects. Therefore, it is widely recognized that utilizing an implantable pump may be beneficial to both a patient and the treating physician.

Many implantable pump designs have been proposed. For example, commonly invented U.S. Pat. No. 4,969,873 ("the '873 patent"), the disclosure of which is hereby incorporated by reference herein, teaches one such design. The '873 is an example of a constant flow pump, which typically include a housing having two chambers, a first chamber for holding the specific medication fluid to be administered and a second chamber for holding a propellant. A flexible membrane may separate the two chambers such that expansion of the propellant in the second chamber pushes the medication fluid out of the first chamber. This type of pump also typically includes an outlet opening connected to a catheter for directing the medication fluid to the desired area of the body, a replenishment opening for allowing for refilling of medication fluid into the first chamber and a bolus opening for allowing the direct introduction of a substance through the catheter without introduction into the first chamber. Both the replenishment opening and the bolus opening are typically covered by a septum that allows a needle or similar device to be passed through it, but properly seals the openings upon removal of the needle. As pumps of this type provide a constant flow of medication fluid to the specific area of the body, they must be refilled periodically with a proper concentration of medication fluid suited for extended release.

Although clearly beneficial to patients and doctors that utilize them, one area in which such constant flow implantable pumps can be improved, is in their overall size. Typically, such pumps require rather bulky outer housings, or casings, for accommodating the aforementioned medication and propellant chambers, and septa associated therewith. Often times, implantable pumps are limited to rather small areas within the body. Depending upon the size of the patient for which the pump is implanted, this limited area may be even further limited. For example, a person having smaller body features, or those containing abnormal anatomy, may present a doctor implanting a constant flow pump with some added difficulty. Further, patients may be uncomfortable having standard sized constant flow pumps implanted in them. Such pumps are often times capable of being felt from the exterior of the patient.

Implantable pumps may also be of the programmable type. Pumps of this type provide variable flow rates, typically through the use of a solenoid pump or a peristaltic pump. In the solenoid pump, the flow rate of medication fluid can be controlled by changing the stroke rate of the pump. In the peristaltic pump, the flow rate can be controlled by changing the roller velocity of the pump. However, both of these types of programmable pumps require intricate designs and complicated controlling mechanisms. As such, it is more desirable to utilize pumps having designs similar to the aforementioned constant flow pumps.

However, the benefit of providing a variable flow rate pump cannot be forgotten. While a constant flow of a medication such as a painkiller may indeed be useful in dulling chronic pain, it is very common for patients to experience more intense pain. At times of this heightened pain, it would be advantageous to be able to vary the flow rate of pain killer to provide for more relief. However, constant flow rate pumps typically may only provide such relief by allowing for direct injections of painkillers or the like through the aforementioned bolus port, which provides direct access to the affirmed area. While indeed useful, this method amounts to nothing more than additional painful injections, something the pump is designed to circumvent.

Therefore, there exists a need for an implantable constant flow pump, which allows for a reduced overall size, as well as an implantable pump that combines the simplistic design of a constant flow rate type pump and means for varying its flow rate, without requiring the use of the complex solutions provided by known programmable pumps.

SUMMARY OF THE INVENTION

A first aspect of the present invention is a reduced size implantable device for dispensing an active substance to a patient. The implantable device of a first embodiment of this first aspect includes a housing defining an active substance chamber in fluid communication with an outlet for delivering the active substance to a target site within the patient and a propellant chamber adjacent the active substance chamber. The implantable device further includes an undulating flexible membrane separating the active substance and propellant chambers, wherein the active substance chamber has an undulating surface including a central convex portion flanked by at least two concave portions, the undulating surface cooperating with the undulating flexible membrane.

In accordance with this first embodiment of the first aspect of the present invention, the propellant chamber may contain a propellant capable of expanding isobarically where the propellant cooperates with the flexible membrane to reduce the volume of the active substance chamber upon expansion of the propellant. The cooperating undulating surface of the active substance chamber and the undulating flexible membrane preferably meet upon complete expansion of the propellant. The implantable device may further include a replenishment opening in the housing in fluid communication with the active substance chamber, and a first septum sealing the opening. The replenishment opening may be located within the central convex portion of the undulating surface of the active substance chamber so as to lower the overall height of the housing of the implantable device. Additionally, the housing may include two portion beings constructed so as to screw together. The two portions may be constructed of PEEK. The two portions may be configured so as to capture the membrane therebetween. Finally, the housing may also include a locking portion and/or a septum retaining member.

A second embodiment of this first aspect of the present invention is yet another implantable device for dispensing an active substance to a patient. The implantable device according to this second embodiment includes a housing defining a chamber and an outlet in fluid communication with the chamber for delivering the active substance to a target site within the patient, the housing having a first portion and a second portion, where the first and second portions are constructed of PEEK and screwed together.

A third embodiment of this first aspect of the present invention is yet another implantable device for dispensing an active substance to a patient. The implantable device according to this third embodiment includes a housing including a top portion, a bottom portion and a locking portion. The housing defines a propellant chamber and an active substance chamber in fluid communication with an outlet. The implantable device preferably also includes a membrane retained between the top and bottom portions, the membrane separating the active substance and propellant chambers. In a fully assembled stated, the top and bottom portions are preferably placed together and the locking portion engages one of the top or bottom portions to retain the top and bottom portions together.

A fourth embodiment of this first aspect of the present invention relates to a method of assembling a reduced size implantable pump. The method of this embodiment includes the steps of placing together a top portion and a bottom portion to retain a membrane therebetween, and screwing a locking portion into the top portion or the bottom portion to retain the top and bottom portions together.

A second aspect of the present invention includes an implantable device for dispensing an active substance to a patient including a housing defining a chamber, said housing having an outlet for delivering the active substance to a target site within the patient, the outlet in fluid communication with the chamber and means for varying the flow rate of the active substance between the chamber and the outlet. The chamber, in accordance with this second aspect of the present invention, may include an active substance chamber in fluid communication with the outlet and a propellant chamber, the active substance and propellant chambers being separated by a flexible membrane. The propellant chamber may contain a propellant capable of expanding isobarically and cooperating with the flexible membrane to reduce the volume of the active substance chamber upon expansion of the propellant. The housing of the implantable device may include an opening in fluid communication with the active substance chamber and a first septum sealing the opening. The housing may further include an annular opening in communication with the outlet and a second septum sealing the annular opening.

In a first embodiment of this second aspect, the means for varying the flow rate of the active substance between the chamber and the outlet may include an elongated polymer filament having a cross sectional dimension. The filament, in accordance with this embodiment, is preferably located in a capillary and is preferably capable of being elongated to reduce the cross sectional dimension. In certain examples, the filament is located centrally within the capillary, in others, it is located eccentrically. The filament may have a uniform cross section, a substantially circular cross section, non-uniform cross section and the like along its length. Further, this first embodiment may further include means for elongating the filament.

In a second embodiment of this second aspect, the means for varying the flow rate of the active substance between the chamber and the outlet may include a first hollow cylinder having a threaded exterior surface and a second hollow cylinder having a threaded interior surface. The first hollow cylinder is axially received within the second hollow cylinder, such that the threaded exterior surface of the first cylinder engages the threaded interior surface of the second cylinder. In this embodiment, the axial movement of the first cylinder with respect to the second cylinder varies the flow rate of the active substance.

In a third embodiment of this second aspect, the means for varying the flow rate of the active substance between the chamber and the outlet may include a hollow tubular element having a cross section that is capable of being varied. This third embodiment may also include a capillary in fluid communication between the chamber and the outlet, where the tubular element is located therein. The hollow tubular element in accordance with this embodiment may be centrally or eccentrically located within the capillary.

In a fourth embodiment of this second aspect, the means for varying the flow rate of the active substance between the chamber and the outlet may include an elongate insert having a longitudinally varying cross section along its length. Movement of this elongate insert may increase or decrease the flow rate of the active substance.

A third aspect of the present invention includes an implantable device for dispensing an active substance to a patient including a housing defining a chamber, said housing having an outlet for delivering the active substance to a target site within the patient, the outlet in fluid communication with the chamber. The implantable device also includes a capillary in fluid communication between the chamber and the outlet, the capillary having an inner surface and a flow control element received within the capillary. The element has an outer surface opposing the inner surface of the capillary defining therebetween a passageway for the flow of the active substance therethrough. The outer surface of the element is preferably movable relative to the inner surface of the capillary to alter the flow of the active substance therethrough. The movement of the outer surface of the element may alter the shape and/or size of the passageway.

In a first embodiment of this third aspect, the means for varying the flow rate of the active substance between the chamber and the outlet may include an elongated polymer filament having a cross sectional dimension. The filament, in accordance with this embodiment, is preferably located in a capillary and is preferably capable of being elongated to reduce the cross sectional dimension. In certain examples, the filament is located centrally within the capillary, in others, it is located eccentrically. The filament may have a uniform cross section, a substantially circular cross section, non-uniform cross section and the like along its length. Further, this first embodiment may further include means for elongating the filament.

In a second embodiment of this third aspect, the means for varying the flow rate of the active substance between the chamber and the outlet may include a first hollow cylinder having a threaded exterior surface and a second hollow cylinder having a threaded interior surface. The first hollow cylinder is axially received within the second hollow cylinder, such that the threaded exterior surface of the first cylinder engages the threaded interior surface of the second cylinder. In this embodiment, the axial movement of the first cylinder with respect to the second cylinder varies the flow rate of the active substance.

In a third embodiment of this third aspect, the means for varying the flow rate of the active substance between the chamber and the outlet may include a hollow tubular element having a cross section that is capable of being varied. This third embodiment may also include a capillary in fluid communication between the chamber and the outlet, where the tubular element is located therein. The hollow tubular element in accordance with this embodiment may be centrally or eccentrically located within the capillary.

In a fourth embodiment of this third aspect, the means for varying the flow rate of the active substance between the chamber and the outlet may include an elongate insert having a longitudinally varying cross section along its length. Movement of this elongate insert may increase or decrease the flow rate of the active substance.

A fourth aspect of the present invention includes a resistor for varying the flow rate of a fluid from a first point to a second point including a capillary having an inner surface and a flow control element received with the capillary. The element has an outer surface opposing the inner surface of the capillary such that a passageway is defined for the flow of fluid therethrough. The outer surface of the element is preferably moveable relative to the inner surface of the capillary to alter the flow of the fluid therethrough. The movement of the outer surface of the element may alter the shape and/or size of the passageway. It is noted that this aspect may be utilized in conjunction with an implantable device such as an implantable pump for delivering a medicament to a site within a patient. Embodiments in accordance with the third aspect are envisioned that are similar to those discussed above in relation to the first and second aspects of the present invention.

A fifth aspect of the present invention includes a method of varying the flow rate of an active substance being dispensed to a patient. This method includes the steps of providing an implantable device including a capillary having an inner surface and a flow control element received within the capillary. The element preferably has an outer surface opposing the inner surface of the capillary such that a passageway for the flow of the active substance therethrough is defined therebetween for dispensing the active substance to a target site within a patient. Further the method includes the step of moving the element relative to the inner surface of the capillary to alter the flow rate of the active substance therethrough. This moving step may alter the size and/or shape of the passageway.

BRIEF DESCRIPTION OF THE DRAWINGS

A more complete appreciation of the subject matter of the present invention and the various advantages thereof can be realized by reference to the following detailed description in which reference is made to the accompanying drawings in which:

FIG. 10a is a longitudinal cross sectional view of the variable flow resistor of FIG. 9, in an initial position.

FIG. 10b is a longitudinal cross sectional view of the variable flow resistor of FIG. 10a, in an extended position.

FIG. 12a is a longitudinal cross sectional view of the variable flow resistor of FIG. 11a, in an initial position.

FIG. 12b is a longitudinal cross sectional view of the variable flow resistor of FIG. 12a, in an extended position.

FIG. 13 is a longitudinal cross sectional view of another variable flow resistor in accordance with the present invention.

FIG. 14 is a longitudinal cross sectional view of another variable flow resistor in accordance with the present invention.

DETAILED DESCRIPTION

In describing the preferred embodiments of the subject matter illustrated and to be described with respect to the drawings, specific terminology will be used for the sake of clarity. However, the invention is not intended to be limited to any specific terms used herein, and it is to be understood that each specific term includes all technical equivalents which operate in a similar manner to accomplish a similar purpose.

Figure 1:
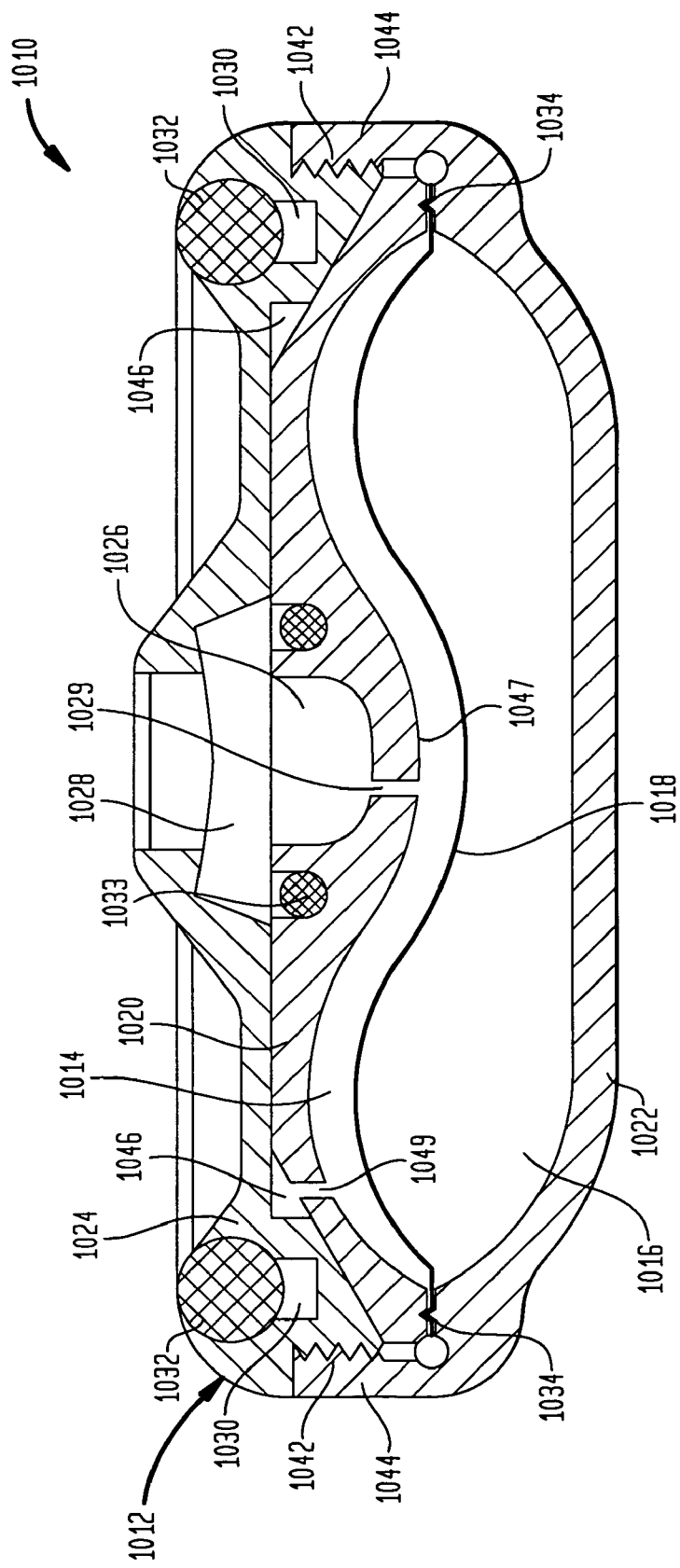
FIG. 1 is a cross sectional front view of a reduced size implantable pump in accordance with one embodiment of the present invention.
Figure 2:
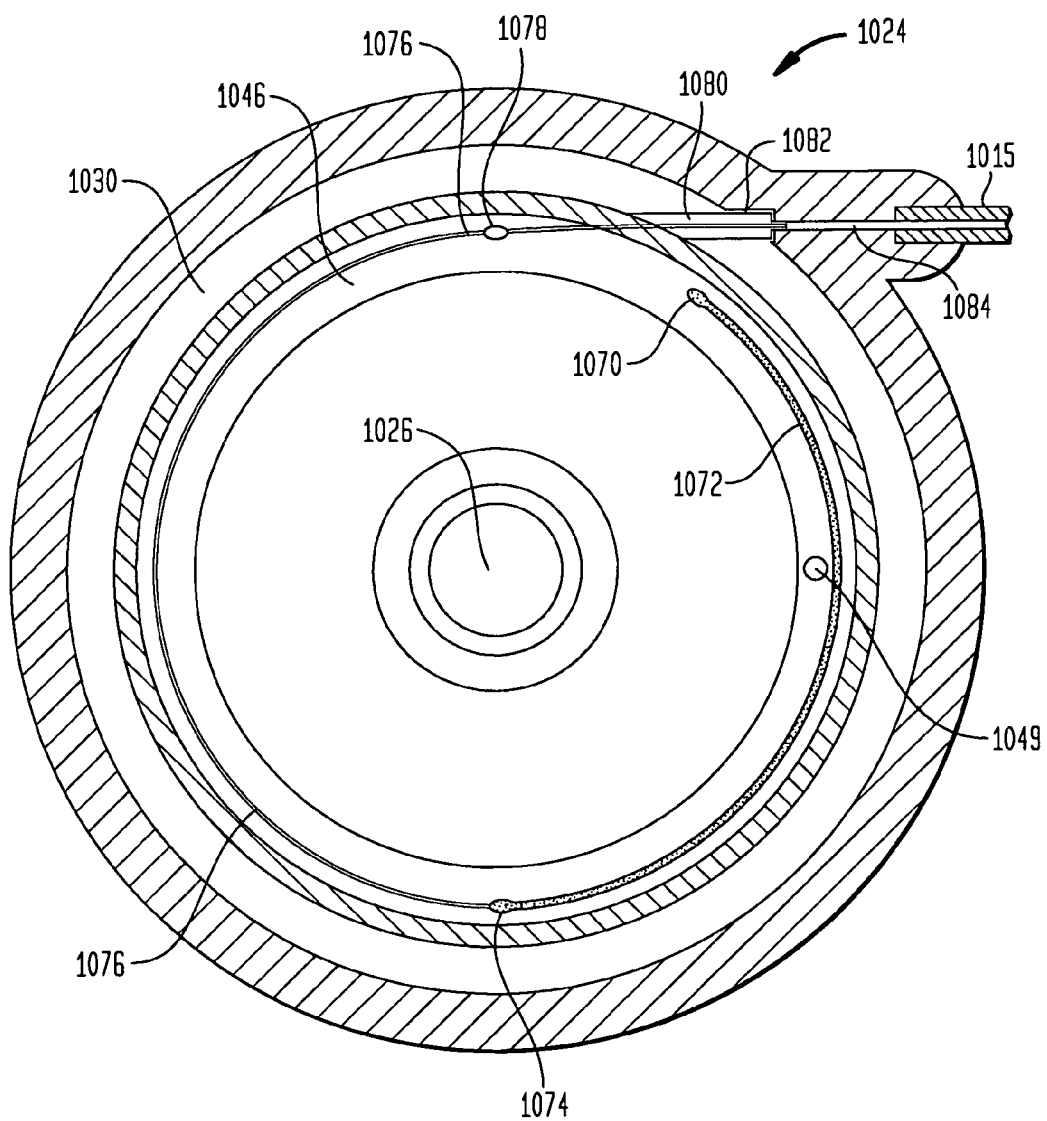
FIG. 2 is a cross sectional bottom view of a portion of the reduced sized implantable pump shown in FIG. 1.

Referring to the drawings, wherein like reference numerals refer to like elements, there is shown in FIGS. 1 and 2, in accordance with various embodiments of the present invention, a reduced size implantable pump designated generally by reference numeral 1010. In a preferred embodiment, pump 1010 is a constant flow pump including a housing 1012, which further defines an interior having two chambers 1014 and 1016. Chambers 1014 and 1016 are preferably separated by a flexible membrane 1018. It is noted that membrane 1018 may be of any design known in the art, for example, a membrane like that disclosed in commonly owned U.S. Pat. No. 5,814,019, the disclosure of which is hereby incorporated by reference herein. In a preferred embodiment, chamber 1014 is designed and configured to receive and house an active substance such as a medication fluid for the relief of pain, treatment of spasticity and neuro-mechanical deficiencies and the administration of chemotherapy, while chamber 1016 may contain a propellant that expands isobarically under constant body heat. This expansion displaces member 1018 such that the medication fluid housed in chamber 1014 is dispensed into the body of the patient through an outlet catheter 1015 (best shown in FIG. 2).

The design and configuration of housing 1012 is such that manufacturing and assembly of pump 1010 is relatively easy. Housing 1012 further includes separately manufactured top portion 1020, bottom portion 1022 and locking portion 1024. It is noted that in certain preferred embodiments, housing 1012 defines a substantially circular pump 1010. However, the housing may ultimately be a pump of any shape. In addition to the above described elements, pump 1010 also preferably includes replenishment port 1026 covered by a first septum 1028 that is in fluid communication with chamber 1014 through a channel 1029, an annular ring bolus port 1030 covered by a second septum 1032, and barium filled silicone o-ring 1033. Each of these elements will be discussed further below.

Referring to both FIGS. 1 and 2, where FIG. 2 is a cross sectional bottom view of locking portion 1024, the flow path of a medication fluid contained within chamber 1014 is shown. Upon the expansion of propellant contained within propellant chamber 1016 and the necessary displacement of membrane 1018, fluid contained in chamber 1014 is forced through an opening 1049 and into a cavity 1046, which will be further described below. As shown in FIG. 2, cavity 1046 extends in a circular fashion around pump 1010. Once in cavity 1046, the fluid may enter at any point along the length of a filter capillary 1072. Essentially, filter capillary 1072 is a well known type filter that allows for fluid to enter into its inner fluid path through permutation or the like. Thus, once a certain amount of fluid builds up within cavity 1046, it is capable of entering into filter 1072. This filter is preferably fixed and sealed in position by drops of glue or other adhesive located at 1070 and 1074. The fluid then travels through filter capillary 1072 until it exits into a resistor 1076. This resistor is preferably a LONG tube having a relatively small diameter, so as to dictate the maximum flow rate that may be achieved therethrough. In other words, the smaller the diameter of resistor 1076, the slower the flow rate of fluid traveling therethrough. Nevertheless, as more fully discussed below, resistor 1076 may be many different types of designs. The fluid within resistor 1076 then continues to an opening 1078 for a bridge 1080, which essentially allows resistor 1076 to cross over bolus port 1030. Thereafter, the fluid may continue through resistor 1076 and ultimately out catheter 1015. Epoxy or another suitable adhesive or sealant may be utilized to seal end 1070, end 1074 and opening 1078. Thus, fluid in cavity 1046 may only follow the path outlined above.

It is noted that FIG. 2 also depicts the flow path that fluid introduced through a bolus injection may take. Fluid may be injected into bolus port 1030 through the use of a device suitable for piercing septum 1032, such as a needle. Once in port 1030, which extends around pump 1010, fluid may enter a channel 1082. This channel extends at least partially around the above mentioned bridge 1080, and allows fluid injected into bolus port 1030 to ultimately exit catheter 1015 without passing through any portion of resistor 1076. As shown in FIG. 2, regardless of the path the fluid takes, it ultimately ends up in a passage 1084 just prior to catheter 1015. Thus, fluid coming from chamber 1014 may have one flow rate, while fluid directly injected into port 1030 may have a different flow rate, the latter preferably being greater.

Figure 3:
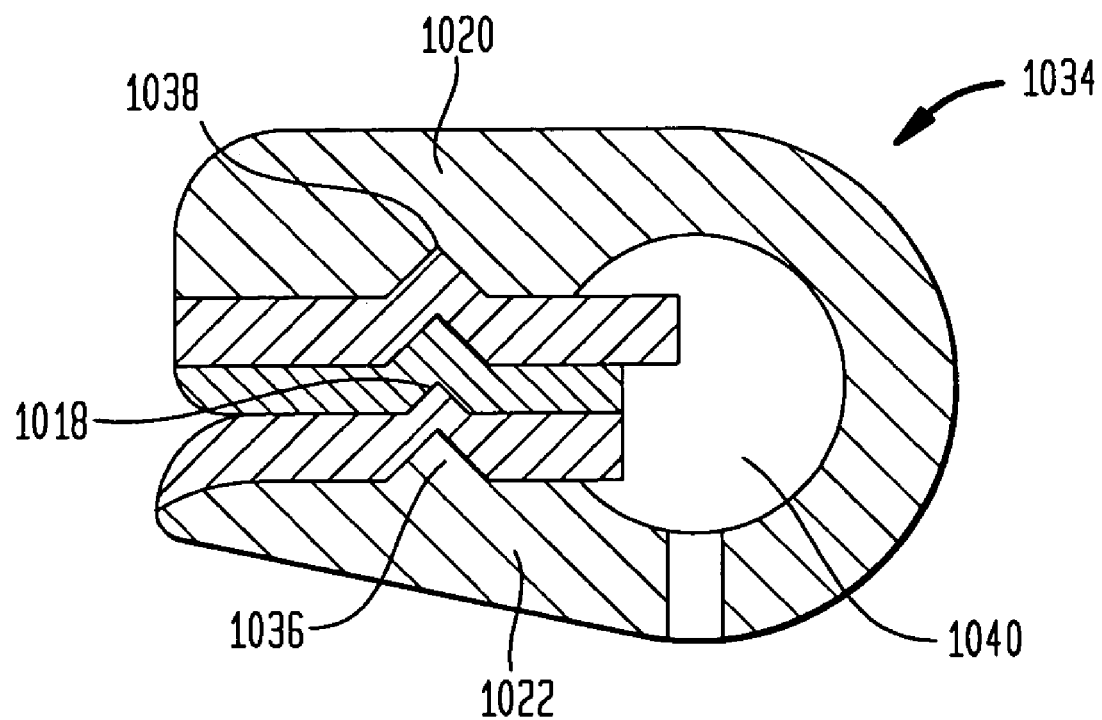
FIG. 3 is an enlarged view of an attachment area of the pump shown in FIG. 1.

The assembly of pump 1010 will now be discussed. It is noted that each of the individual elements/components of pump 1010 may be individually manufactured and thereafter assembled by hand or by another process, such as an automated process. As an initial step, top portion 1020 and bottom portion 1022 are placed or sandwiched together so as to capture membrane 1018 therebetween in an attachment area 1034 for fixably retaining same. As more clearly shown in the enlarged view of FIG. 3, attachment area 1034 comprises a projection 1036 located on bottom portion 1022, a depression 1038 located on top portion 1020, and a cavity 1040 formed through the cooperation of the two portions. In operation, the step of sandwiching together portions 1020 and 1022, with membrane 1018 disposed therebetween, causes projection 1036 to be forced into depression 1038. The portion of membrane 1018 disposed therebetween is thus also forced into depression 1038 by projection 1036. This causes a crimp-like connection, which fixably attaches and retains membrane 1018 within housing 1012. As shown in FIG. 3, membrane 1018 may consist of multiple layers, of which all are preferably "crimped" during the attachment process. Prior to pressing together portions 1020 and 1022, a layer of epoxy or other adhesive may be inserted into cavity 1040. In such embodiments that employ the use of an adhesive, the design may cause portions 1020 and 1022 to become fixably attached to one another upon the sandwiching of same. Further, the use of an adhesive within cavity 1040 may also aid in the fixation of membrane 1018 between the two portions. The epoxy or other adhesive may be placed into the cavity portion formed on either portion 1020 or portion 1022, prior to the sandwiching step.

Prior or subsequent to the assembly of top portion 1020 together with bottom portion 1022, o-ring 1033 or the like may be placed into a ring-shaped cavity formed in top portion 1022. In certain preferred embodiments, o-ring 1033 is a barium filled silicone o-ring, and is disposed around the area defining replenishment port 1026. Such an o-ring design allows for the area defining replenishment port 1026 to be illuminated under certain scanning processes, such as X-rays. As pump 1010 is implanted within the human body, locating port 1026, in order to refill the pump with medicament or the like, may be difficult. Providing a barium filled o-ring 1033, which essentially outlines the area of port 1026, allows for a doctor to easily locate the desired area under well known scanning processes. Other structures may be utilized, in which same also show up on different scans. The placement of o-ring 1033 is preferably accomplished by pressing the o-ring into an undersized channel that retains the o-ring, thereafter.

With o-ring 1033 preferably in place, locking portion 1024 is next attached to the other portions. It is noted that prior to attaching portion 1024, first septum 1028 should be inserted into locking portion 1024. Preferably, first septum 1028 is slid into a complimentary cavity formed in portion 1024, such that it remains within absent a force acting upon same. As first septum 1028 is designed to be captured between locking portion 1024 and top portion 1020, the septum should be placed prior to the attachment of locking portion 1024. In addition, as mentioned above, locking portion 1024 may include a second septum 1032 for covering bolus port 1030. In certain preferred embodiments, as shown in FIG. 1, second septum 1032 is ring shaped, and is pressed into locking portion 1024 in a similar fashion to that discussed above with relation to the placement of o-ring 1033. This may be done prior or subsequent to the attachment of locking portion 1024 to the other portions.

With regard to the attachment step, locking portion 1024 preferably includes a threaded area 1042 for cooperating with a threaded extension 1044. In operation, locking portion 1024 is merely screwed into engagement with bottom portion 1022. This necessarily causes top portion 1020, which is disposed between the two other portions, to be retained therebetween. In other words, the screw attachment of locking portion 1024 with bottom portion 1022 not only causes such portions to be fixably attached to one another, but also causes top portion 1020 to be fixably retained therebetween. It is noted that, depending upon how tight locking portion 1024 is screwed into 1022, portions 1020 and 1022 may be further pressed together, thereby increasing the fixation of membrane 1018 therebetween. Thus, pump 1010 is designed so that minimal connection steps are performed in order to cause all of the components thereof to be retained together. It is further noted that, in addition to the above discussed screw connection of portions 1022 and 1024, other attachment means may be utilized. For example, such portions may be snap fit together or fixed utilizing an adhesive. Finally, locking portion 1024 may be configured so as to form cavity 1046 between itself and top portion 1020. This cavity may be designed so as to allow for the injection of adhesive therein, thus increasing the level of fixation between the different portions of housing 1012. Additionally, cavity 1046 may house a flow resistor or the like, as will be more fully discussed below.

As set forth above, pump 1010 is configured and dimensioned to be relatively simplistic in both manufacture and assembly. However, pump 1010 is also configured and dimensioned so as to employ a significantly reduced overall size, while still providing for a useful amount of medicament and propellant to be housed therein. In the preferred embodiments depicted in the figures, top portion 1020 of pump 1010 includes an interior surface 1047 having an undulating or convoluted shape. More particularly, surface 1047 includes a convex central portion flanked by two concave portions. This configuration allows for the centrally located replenishment port 1026 and cooperating septum 1028 to be situated in a lower position with respect to the remainder of pump 1010. At the same time, the aforementioned flanking concave portions allow for the overall volume of chambers 1014 and 1016 to remain substantially the same as a pump employing an interior surface having one constant concave portion or the like. In other words, the flanking concave portions make up for the volume lost in situating port 1026 and cooperating septum 1028 in a lower position. Membrane 1018 is also preferably configured so as to have an initial undulating shape for cooperation with interior surface 1047. Thus, with no medicament or other fluid located within chamber 1014, membrane 1018 preferably rests against surface 1047. However, upon injection of fluid into chamber 1014, membrane 1018 adapts to the position shown in FIG. 1.

Figure 4:
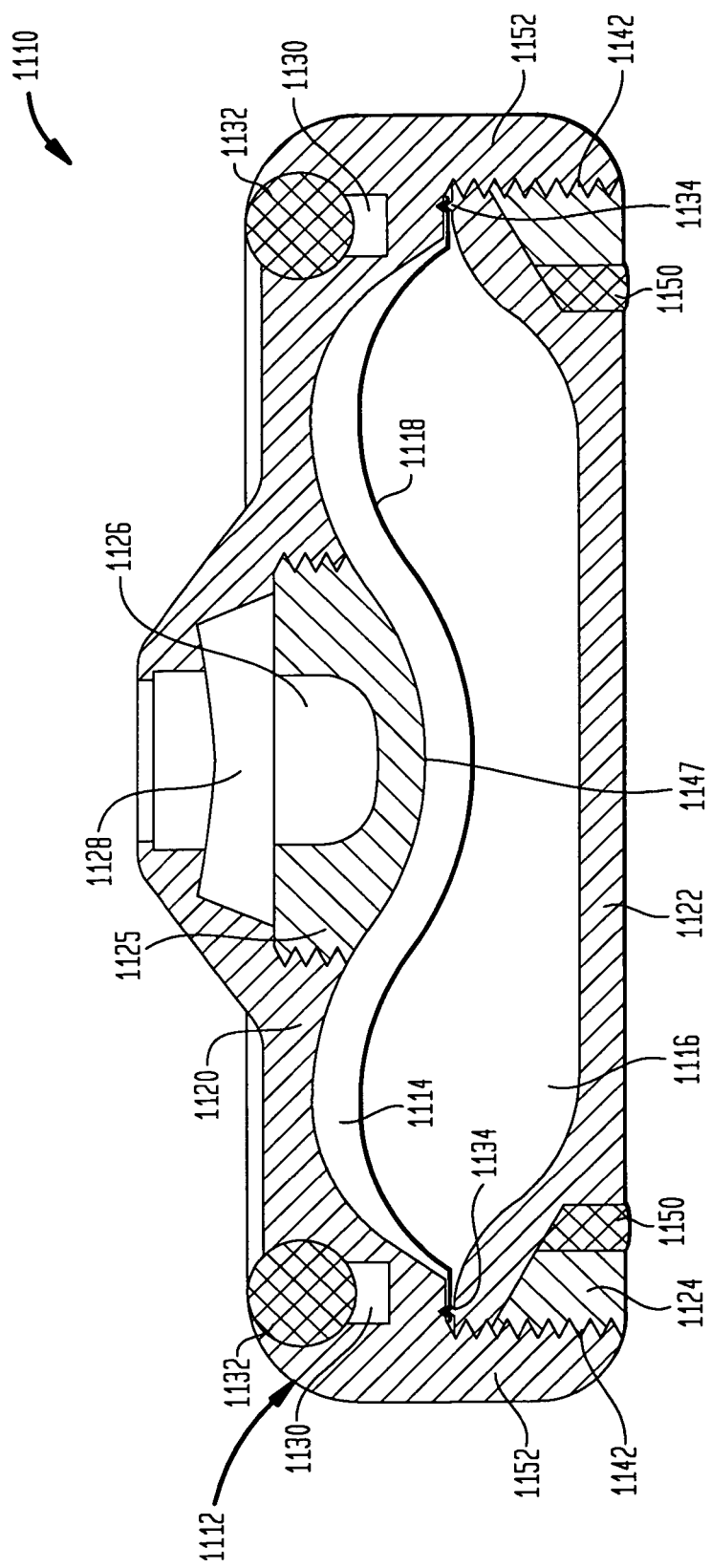
FIG. 4 is a cross section front view of a reduced size implantable pump in accordance with another embodiment of the present invention.

FIG. 4 depicts another reduced sized implantable pump designated by reference numeral 1110. As shown in the figure, pump 1110 includes several elements which are similar in structure and function to that of pump 1010. These elements are labeled with like references numerals within the 1100 series of numbers. For example, membrane 1118 is similar to the above described membrane 1018. In addition, pump 1110 operates in a similar fashion to that of pump 1010. Nevertheless, pump 1110 does include certain additional elements, as well as elements employing different constructions. Most notably, pump 1110 includes an additional component, namely septum retaining member 1125. This member is preferably adapted to be screwed into top portion 1120. Pump 1110 also includes a bottom o-ring 1150, but does not include a barium filled o-ring.

The assembly of pump 1110 also differs from that of pump 1010. As briefly mentioned above, initially, septum retaining member 1125 is first screwed into top portion 1120 in order to retain previously placed septum 1128 in place. Like the above described assembly of pump 1010, the assembly of pump 1110 then includes the step of sandwiching together portions 1120 and 1122, where membrane 1118 is likewise captured therebetween in attachment area 1134. However, in this embodiment, locking portion 1124 is adapted to engage top portion 1120, so that it is positioned on the bottom side of pump 1110. As shown in FIG. 4, top portion 1120 includes a threaded extension 1152 to cooperate and engage with threaded area 1142 of locking portion 1124. The screw connection between the two portions is similarly achieved. However, bottom o-ring 1150 is preferably situated between locking portion 1124 and bottom portion 1122. This o-ring both increases the force exerted on bottom portion 1122 by locking portion 1124, and also causes housing 1112 to retain a smooth exterior surface. The latter is important in implanting the pump within a patient, as rough or jagged surfaces may cause damage to tissue abutting the pump. Finally, it is noted that second septum 1132 may be pressed into top portion 1120, at any point during the assembly.

Figure 5:
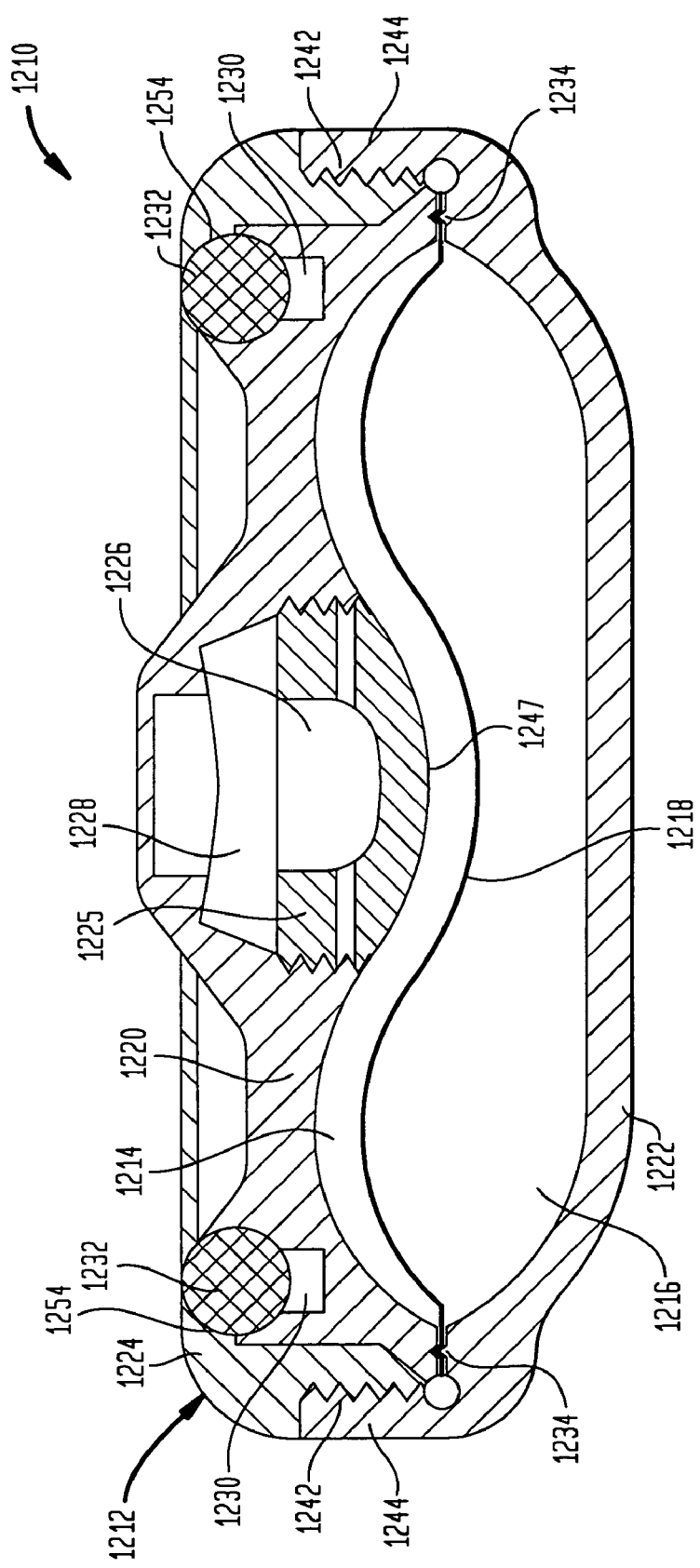
FIG. 5 is a cross section front view of a reduced size implantable pump in accordance with another embodiment of the present invention.

FIG. 5 depicts another reduced sized implantable pump designated by reference numeral 1210. As shown in that figure, pump 1210 includes several elements which are similar in structure and function to that of pumps 1010 and 1110. Once again, these elements are labeled with like reference numerals within the 1200 series of numbers. Nevertheless, pump 1210 does include certain additional elements, as well as elements employing different constructions. For example, like pump 1110, pump 1210 includes a septum retaining member 1225. Similarly, like pump 1010, pump 1210 utilizes a top mounting locking portion 1224, although it has a different construction.

The assembly of pump 1210 differs from that of the above discussed pumps 1010 and 1110. Like pump 1110, septum retaining member 1225 is first screwed into top portion 1220, in order to retain previously placed septum 1228 in place. Next, portions 1120 and 1222 are sandwiched together, thus capturing member 1218 within attachment 1234. Finally, locking portion 1224 is screwed into engagement with bottom portion 1222. Like the design of pump 1010, locking portion 1224 includes a threaded area 1242 which engages a threaded extension 1244 of bottom portion 1222. In addition to completing the assembly of pump 1210 by capturing bottom portion 1222 and forcing top portion 1220 towards bottom portion 1222, locking portion 1224 is configured and dimensioned in this embodiment to also capture second septum 1232. As shown in FIG. 5, locking portion 1224 includes a concave section 1254 for engaging septum 1232 upon the full engagement of portions 1222 and 1224.

Figure 6:
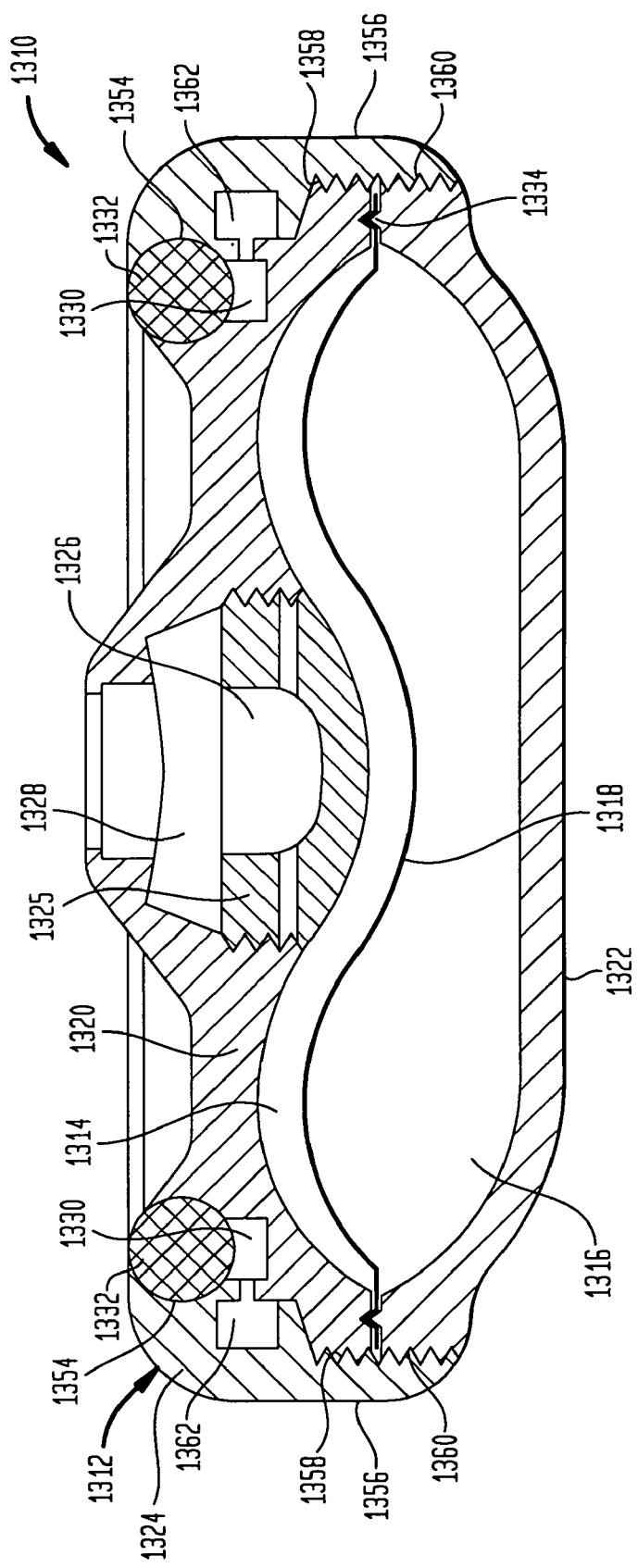
FIG. 6 is a cross section front view of a reduced size implantable pump in accordance with another embodiment of the present invention.

Yet another embodiment reduced sized pump 1310 is shown in FIG. 6. Like those pumps discussed above, pump 1310 preferably includes several elements which are similar in structure and function, and are thus labeled with like reference numerals within the 1300 series of numbers. Essentially, pump 1310 is akin to the configuration set forth in pump 1210. However, there are two main distinctions, namely, the cooperation of locking portion 1324 and portions 1320 and 1322, and the inclusion of a channel 1362 between locking portion 1324 and top portion 1320. In the embodiment depicted in FIG. 6, it is noted that locking portion 1324 includes a threaded extension 1356, which cooperate and engage threaded areas 1358 and 1360 of portions 1320 and 1322, respectively. Furthermore, locking portion 1324 preferably includes a channel 1362 formed therein. This channel may be adapted to cooperate with any of the chambers and/or ports discussed above. Additionally, channel 1362 may house other elements, such as a flow resistor or the like, which will be discussed more fully below.

Figure 7:
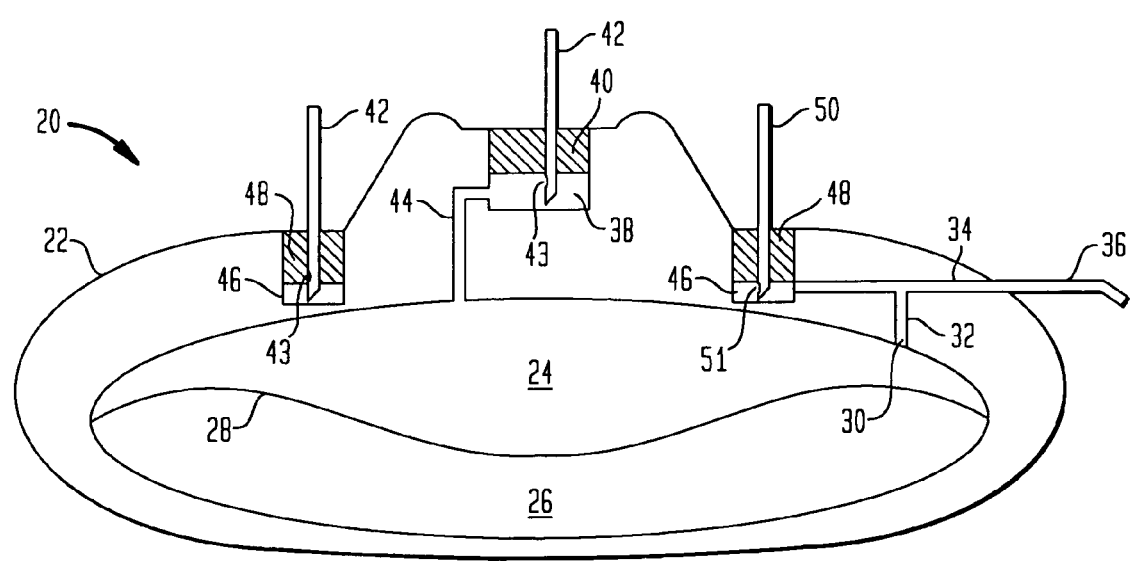
FIG. 7 is a cross sectional front view of an implantable constant flow pump for use in accordance with the present invention.

A second aspect of the present invention relates to providing a constant flow type implantable pump with infinitely variable flow capabilities. As mentioned above, such a construction may be beneficial to patients requiring more or less medication to be delivered by an implantable pump. While the different embodiments of this second aspect of the present invention may indeed be sized and configured to be utilized with any constant flow type implantable pump, preferred pumps will be described herein. In one preferred pump, as shown in FIG. 7 of the present application, the basic implantable pump design is designated as reference numeral 20. Pump 20 includes a housing 22 defining an interior having two chambers 24 and 26. Chambers 24 and 26 are separated by a flexible membrane 28. Chamber 24 is designed to receive and house the active substance such as a medication fluid for the relief of pain, treatment of spasticity and neuro-mechanical deficiencies and the administration of chemotherapy, while chamber 26 may contain a propellant that expands isobarically under constant body heat. This expansion displaces membrane 28 such that the medication fluid housed in chamber 24 is dispensed into the body of the patient through the path defined by an outlet opening 30, a resistor 32, an outlet duct 34 and ultimately an outlet catheter 36.

Resistor 32 provides a connection between chamber 24 and outlet duct 34. Thus, as mentioned above, a medication fluid flowing from chamber 24 to outlet catheter 36 must necessarily pass through resistor 32. This resistor allows for the control of the flow rate of the medication fluid, such that the flow rate is capable of being varied. Resistor 32 may be configured differently in many different embodiments, some of which are discussed below in the detailed description of the present invention. Essentially, resistor 32 defines a passageway for the flow of the medication fluid, where the passageway may be altered to thereby alter the flow rate of the medication fluid.

Implantable pump 20 also includes a replenishment port 38 covered by a first septum 40. Septum 40 can be pierced by an injection needle (such as needle 42 shown in FIG. 7) and, upon removal of such needle, is capable of automatically resealing itself. Septa of this type are well known to those of ordinary skill in the art. As implantable pump 20 is designed to medicate a patient over a limited period of time, replenishment port 38 is utilized for replenishing chamber 24 when empty or near empty. In operation, a physician or other medical professional inserts an injection needle 42 into an area of a patient's body where pump 20 is located, such that it may pierce septum 40. Thereafter, operation of the needle causes injection of the solution from the needle to pass into port 38, through passage 44, and into chamber 24. It is noted that the particular dimension and/or the patient's need may require such a process to be repeated at given intervals, for example, monthly, weekly, etc.

In addition to replenishment port 38, pump 20 also includes an annular ring bolus port 46 covered by a second septum 48. Essentially, this port allows for direct introduction of a solution into outlet catheter 36 and to the specific target area of the body. This port is particularly useful when a patient requires additional or stronger medication, such as a single bolus injection, and/or when it is desired to test the flow path of catheter 36. Such an injection is performed in a similar fashion to the above discussed injection into replenishment port 38. However, an injection into bolus port 46 bypasses passage 44, chamber 24 and resistor 32, and provides direct access to catheter 36. It is also contemplated to utilize bolus port 46 to withdraw fluid from the body. For example, where pump 20 is situated within the body such that catheter 36 extends to the vertebral portion of the spinal column, a needle with a syringe connected may be inserted into bolus portion 46 and operated to pull spinal fluid through catheter 36 and into the syringe.

In certain embodiments, septum 40 and septum 48 may be situated so that only specifically designed injection needles may be used to inject into the respective ports. For example, as is also shown in FIG. 7, septum 48 may be situated relatively close to the bottom of port 46 and septum 40 may be situated a greater distance away from the bottom of port 38. In this embodiment, injection needle 42 is provided with an injection eye 43, which is located above the tip of needle 42. Alternatively, injection needle 50 is provided with an injection eye 51 located at or near its tip. This arrangement prevents needle 42, which is typically utilized for replenishing chamber 24 with a long term supply of medication fluid, from being inadvertently used to inject its contents into bolus port 46. As is shown on the left side depiction of bolus port 46, needle 42 would have its eye 43 blocked by septum 48 if the needle is inadvertently inserted into this port. Needle 50, on the other hand, would be capable of injecting into port 46 because of the lower location of its eye 51. This is an important safety feature, as direct injection of a long term supply of medication fluid into port 46 could be dangerous. It is noted that needle 50 is also capable of injecting a solution into replenishment port 38, however, the same concerns (i.e.—over-medication) do not exist with respect to the filling of chamber 24, and as such medication housed in the chamber is slowly released. While this is one example of a possible safety feature with regard to the injection of materials into the pump, it is envisioned that other safety precautions may be utilized. For example, U.S. Pat. No. 5,575,770, the disclosure of which is hereby incorporated by reference herein, teaches a similar multiple injection needle system with additional valve protection. It is noted that such a safety needle system may be employed with regard to any of the various implantable pump embodiments disclosed herein. One of ordinary skill in the art would recognize the modifications required to utilize such a safety feature in the other discussed pump designs.

Figure 8:
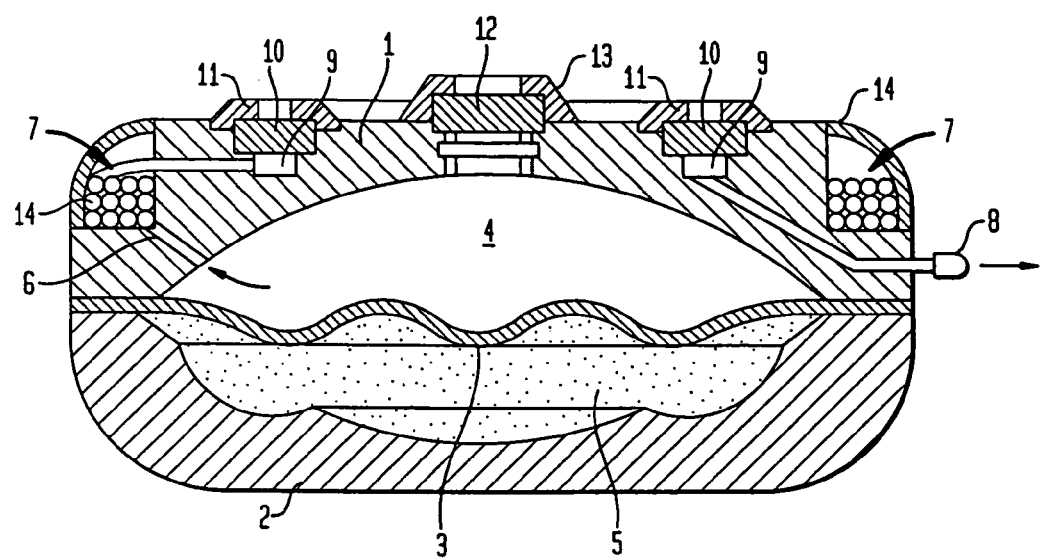
FIG. 8 is a cross sectional front view of another implantable constant flow pump for use in accordance with the present invention.

In other embodiments, the basic implantable pump design of the aforementioned '873 patent may also be utilized. As is discussed in its specification and shown in FIG. 8 of the present application, the '873 patent discloses a housing made up of two parts 1, 2 and an interior having two chambers 4, 5, which are separated by a flexible membrane 3. Chamber 4 is designed to receive and house the medication fluid, while chamber 5 may contain a propellant which, like that discussed in the above description of pump 20, expands isobarically under constant body heat. This expansion displaces membrane 3 such that the medication fluid housed in chamber 4 is dispensed into the body of the patient through the path defined by an outlet opening 6, an outlet reducing means 7 and ultimately an outlet catheter 8. It is noted that reducing means 7 is preferably a tube winding that wraps around part 1 of the housing. The resistor of the present invention, in certain embodiments, is preferably located at or near outlet opening 6. This will be discussed more fully below.

Prior to reaching outlet catheter 8, the medication fluid is introduced into a chamber 9 which is provided annularly on part 1 of the housing. Chamber 9 is sealed at its upper side by a ring or septum 10, which can be pierced by an injection needle and which automatically reseals upon withdrawal of the needle. This chamber is similar to the above discussed bolus port 46 of pump 20. In addition to allowing medication fluid from chamber 4 to pass into outlet catheter 8, chamber 9 also allows the direct injection of a solution into outlet catheter 8, the importance of which is discussed above. The aforementioned outlet reducing means 7 prevents a solution injected into the bolus port from flowing into chamber 4. In a similar fashion, when need be, chamber 4 may be replenished via a further septum 12. Once again an injection needle may be utilized for this purpose.

While two basic designs of implantable pumps are described above, it is noted that other designs may include different or additional elements. Similarly, while the above description teaches two implantable pumps that may be utilized in accordance with the present invention, other implantable pump designs are also capable of being utilized. For example, U.S. Pat. Nos. 5,085,656, 5,336,194, 5,722,957, 5,814,019, 5,766,150, 5,836,915 and 6,730,060, the disclosures of which are all hereby incorporated by reference herein, may be employed in accordance with the present invention. In addition, one specific embodiment will be discussed below.

As mentioned above, the capability of varying the flow rate of an implantable pump is desired. In the above discussed constant flow pumps, the flow rate of the medication fluid depends upon the pump pressure, the pressure at the end of the catheter and the hydraulic resistance of any of the capillaries or other passages that the medication fluid must travel through. With regard to the resistance of the capillaries, such resistance depends upon the geometry of the capillary itself, as well as the viscosity of the medication fluid. This viscosity, as well as the pump pressure, may both be influenced by body temperature. As such, one instance in which it is desired to control the flow rate of the pump exists if the patient develops a fever because the flow rate of the infusion device may be affected in an undesired way.

Another example of when the variable flow rate of the implantable pump is desired relates to the condition or active status of the patient. For example, especially in the case where painkillers are being administered, it may be advantageous to deliver less medication during the nighttime hours, when the patient is sleeping. Additionally, as discussed above, it may be desirable to be able to increase the dosage of such painkillers or the like when the patient's symptoms worsen. Increasing of the flow rate of the medication fluid may be necessary in order to diminish the patient's pain level. In accordance with the present invention, the aforementioned resistor 32 is useful for adjusting the flow rate in order to counteract undesirable flow rate changes due to body temperature changes, and to allow for desired adjustments of flow rate to treat heightened or worsened symptoms.

In a first embodiment this adjustment of flow rate is realized by adjusting the cross-sectional geometry of an article of the resistor. It is noted that the first embodiment will be discussed with respect to pump 20; however, it may be utilized in combination with any implantable pump. As shown in FIGS. 9-15, in accordance with this first embodiment, resistor 32 includes an elastic and resilient filament 52 situated in a resistor capillary 54, where resistor capillary 54 provides a connection between outlet opening 30 and outlet capillary 34. Capillary 54 may be situated so as to constitute substantially the entire outlet capillary 34, or may only be a portion thereof. Essentially, capillary 54 need only require the aforementioned medication fluid to pass therethrough, and thus, may be any length suitable for use in varying the flow rate.

Figure 9:
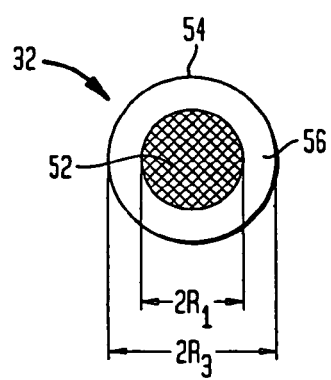
FIG. 9 is a cross sectional view of a variable flow resistor in accordance with a first embodiment of the present invention having a filament located concentrically in a capillary.

FIGS. 9, 10a and 10b show a first example of the first embodiment resistor 32, where elastic filament 52 is located concentrically in resistor capillary 54. This configuration forms a ring-shaped flow channel 56 through which fluid flows in a direction shown by arrow F. As is best shown in FIG. 10a, filament 52 includes a first end 58 attached to a stationary attachment 60, and a second end 62 attached to a movable attachment 64. Resistor 32 also has an effective length L extending between capillary entrance 66 to exit 68, and an initial diameter D1 (i.e.—2 times its radius R1). Additionally, capillary 54 has a diameter D3 (i.e.—2 times its radius R3). This will be similar throughout in the various other capillaries discussed herein.

In this example, movable attachment 64 is capable of moving in the opposite longitudinal directions shown by arrows A and B, while attachment 60 remains stationary. In operation, movement of attachment 64 in the direction of arrow B increases the distance between attachments 62 and 64 and also results in the decrease of the initial diameter D1 to a lesser diameter D2 (i.e.—2 times its lesser radius R2). This is best shown in FIG. 10b. The decrease of the diameter of filament 52 from D1 to D2 increases the size of channel 56 and thus necessarily decreases the hydraulic resistance in capillary 54. Oppositely, movement of attachment 64 in the direction of arrow A returns filament 52 to the position shown in FIG. 10a, and increases the hydraulic resistance in capillary 54. A filament of this type may be constructed of silicone rubber, or other suitable polymer materials for providing the required elasticity and resiliency so as to return to its original shape and size after being deformed by stretching. Similarly, although filament 52 is shown in the figures as having a substantially circular cross section, it is envisioned that filaments having other cross sections may be utilized, for example, polygonal, oval, square and the like.

As the inner diameter of capillary 54 is typically very small (on the order of several thousands of millimeters), it is often difficult to locate filament 52 directly in the center of the capillary. FIGS. 11a, 11b, 12a and 12b depict a second example where elastic filament 52 touches the inner wall of capillary 54 (i.e.—an eccentric position). This eccentrically placed filament 52 creates a sickle-shaped flow channel 56, as opposed to the ring-shaped flow channel of the first example. This second example also differs from the first example discussed above, in that both ends 58, 62 of filament 52 are attached to movable attachments 60, 64, respectively. This is useful, as in operation, one movable attachment (or the mechanism moving it) may fail. The two movable attachment design provides a failsafe, thereby allowing filament 52 to be stretched through the movement of the non-failing attachment. Attachment 64 is still capable of moving in the direction depicted by arrows A and B and attachment 60 is capable of moving in the direction depicted by arrows A' and B'.

In operation, movement of either of attachments 60, 64 in the directions B' and B, respectively, decreases the diameter D1 to a lesser diameter D2 (once again, these diameters refer to two times the radii R1 and R2, respectively). This position is best shown in FIG. 12b. Like that of the above discussed first example, this decrease in the diameter of filament 52 from D1 to D2 increases the size of channel 56 and thus necessarily decreases the hydraulic resistance in capillary 54. Oppositely, movement of either of attachments 60, 64 in the direction of arrows A' and A, respectively, returns filament 52 to the position shown in FIG. 12a, and increases the hydraulic resistance in capillary 54.

Attachment 64 in the first example, and attachments 60, 64 in the second example may be moved by any means known to those of ordinary skill in the art. For example, it is well known to utilize micro-motors, magnets, or other hydraulic, electrical or mechanical actuators. One example of a suitable motor assembly is sold under the designation X15G by Elliptec Resonant Actuator of Dortmund, Germany.

In accordance with the present invention, it is known to design a capillary with a circular lumen defined by a rigid wall. Essentially, this type of apparatus is a hollow tube having a flow therethrough (i.e.—the present design without filament 52). For such a design, the flow rate can be calculated using the well-known Hagen-Poisseuille Equation:

$$V = (\Delta p \pi R_2^4)/(8\eta L)$$

Where:
V=flow rate
$\Delta p$=pressure difference between entrance 66 and exit 68 of capillary 54.
$\eta$=viscosity of fluid.
L=effective length L of resistor 32.
$R_2$=radius of resistor capillary 54 (see in FIG. 9).

As shown in the above equation, small changes in the diameter of a capillary have a profound effect on the flow rate. However, the modification of the $R_2$ dimension is often technically very difficult to realize. Thus, as discussed above, the design of this first embodiment of the present invention includes implementing elastic filament 52 into resistor capillary 54, as discussed above. For the first example of the first embodiment (i.e.—concentrically located filament 52), the following equation may be utilized in determining the flow rate of this design:

$$V = [(\Delta p \pi)(R_2 - R_1)^3(R_2 + R_1)]/(8\Theta L)$$

Where:
V=flow rate
$\Delta p$=pressure difference between entrance 66 and exit 68 of capillary 54.
$\eta$=viscosity of fluid.
L=effective length L of resistor 32.
$R_1$=radius of filament 52 (see in FIG. 9).
$R_2$=radius of resistor capillary 54 (see in FIG. 9).

Alternatively, for the second example of the first embodiment (i.e.—eccentrically located filament 52), the following equation may be utilized in determining the flow rate of this design:

$$V = [(\Delta p \pi)(R_2 - R_1)^3(R_2 + R_1)2.5]/(8\Theta L)$$

Where:
V=flow rate
$\Delta p$=pressure difference between entrance 66 and exit 68 of capillary 54.
$\eta$=viscosity of fluid.
L=effective length L of resistor 32.
$R_1$=radius of filament 52 (see in FIG. 9).
$R_2$=radius of resistor capillary 54 (see in FIG. 9).

All three of the above equations are well known in the field of fluid dynamics. Further, while the effective length L of resistor 32, as best shown in FIGS. 10a and 12a, corresponds to the length of capillary 54, it is noted that the effective length more specifically relates to the length of capillary 54 in which filament 52 resides. Therefore, the effective length L, for use in the above equations, may be less than the length of capillary 54 if filament 52 has a length less than the length of capillary 54. It is noted that these equations apply to the use of capillaries and filaments having circular cross sections. Other embodiments may utilize differently shaped capillaries and filaments. For these embodiments, separate equations must be utilized.

Figure 11A:
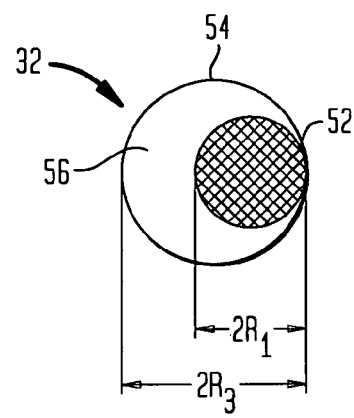
FIG. 11a is a cross sectional view of a variable flow resistor of the present invention having a filament located eccentrically in a capillary.
Figure 11B:
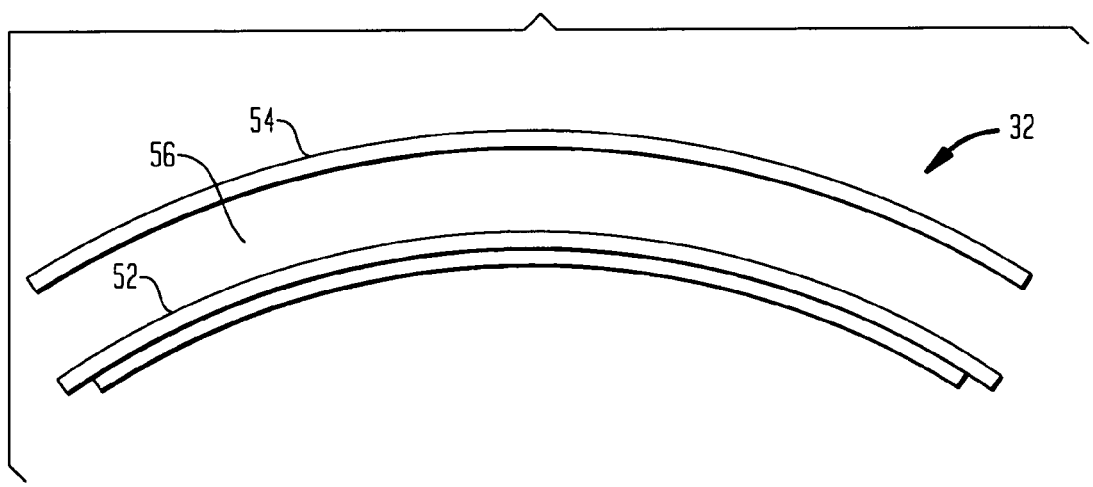
FIG. 11b is a longitudinal cross sectional view of the variable flow resistor of FIG. 11a, depicting the curvature of the capillary.

As is clearly shown by the second equation, situating filament 52 in the offset position with relation to the center of capillary 54 of, as shown in FIG. 11a, allows the flow rate to be changed by a factor of 2.5. Therefore, for applications where it is desired to vary the flow rate by such a ratio, it is possible to merely move filament 52 from a central position taught in the first example (as shown in FIG. 9) to the eccentric position taught in the second example (as shown in FIG. 11a). However, often times, it is typically desired to vary the flow rate by a factor of 25 or more. In order to achieve such a flow rate change, one may utilize an elastic filament 52 as discussed above, situated in an offset position. Typically, to ensure that filament 52 remains in the offset position, a curved capillary 54 is utilized. As shown in FIG. 11b, filament 52 remains eccentrically placed within capillary 54 because of the curvature of the capillary. As filament 52 is generally elastic and resilient, it easily conforms to any curvature of capillary 54.

A realistic range for the change in diameter of elastic filament 52 is approximately from its original size to about seventy percent of its original size (i.e.—a 1 to 0.7 ratio). Calculations have been carried out using the above equation relating to the eccentrically positioned filament 52. For example, with the initial radius R1 of filament 52 being approximately eighty percent (80%) of the radius R2 of capillary 54 (i.e.—a 0.8 to 1 ratio) and the maximal elongation of filament 52 giving a radius R3 that is approximately fifty six percent (56%) of the radius R2 of capillary 54 (i.e.—a 0.56 to 1 ratio), it was calculated the ratio of flow rate between the non-elongated state and the maximal elongated state is approximately 9.20 to 1. With the initial radius R1 of filament 52 being approximately eighty five percent (85%) of the radius R2 of capillary 54 (i.e.—a 0.85 to 1 ratio) and the maximal elongation of filament 52 giving a radius R3 that is approximately fifty nine point five percent (59.5%) of the radius R2 of capillary 54 (i.e.—a 0.595 to 1 ratio), it was calculated the ratio of flow rate between the non-elongated state and the maximal elongated state is approximately 17.00 to 1. Finally, with the initial radius R1 of filament 52 being approximately ninety percent (90%) of the radius R2 of capillary 54 (i.e.—a 0.9 to 1 ratio) and the maximal elongation of filament 52 giving a radius R3 that is approximately sixty three percent (63%) of the radius R2 of capillary 54 (i.e.—a 0.63 to 1 ratio), it was calculated the ratio of flow rate between the non-elongated state and the maximal elongated state is approximately 43.46 to 1. Thus, using a filament 52 having a radius R1 between approximately eighty five percent (85%) and ninety percent (90%) of the total radius R2 of capillary 54, would result in a flow rate variation of approximately 25. From the foregoing, one can calculate the desired flow rate variation based on the known geometry of the flow resistor.

A third example of the first embodiment of the present invention is shown in FIG. 13. This example includes a capillary 154 that is divided into two sectors by a center wall 155. Fluid is capable of flowing through capillary 154 by entering through entrance 166 and exiting through exit 168, as depicted by fluid flow arrow F. An elastic filament 152 is fixed at its ends by fixation points 160 and 164, and is wrapped around a magnetic element 170 at the approximate central portion of filament 152. Repulsive magnetic forces are transmitted to magnetic element 170 by a corresponding magnetic counterpart 172, having a similar polarity. Thus, movement of counterpart 172 results in the like movement of element 170. Counterpart 172 may be located in a hermetically sealed housing 174, or the like. Movement of the magnetic element in a direction indicated by arrow B will, as in the above discussed examples, cause the diameter of filament 152 to shrink, thereby allowing for the increase in flow rate. Similarly, movement of element 170 in the direction indicated by arrow A will decrease the flow rate. It is noted that this two sector design includes two capillary and filament relationships for use in varying the flow rate. As such, where both the capillary and the filament have circular cross sections, two separate calculations in accordance with the above discussed equations, must be conducted to determine the overall hydraulic resistance provided by the system.

Further, in accordance with this third example of the first embodiment, it is envisioned that magnetic element 170 and magnetic counterpart 172 may be oppositely polarized, such that they are attracted to one another. In this type of design, moving counterpart 172 in a direction closer to element 170 would cause the attraction between them to be greater. Thus, if counterpart 172 is located below element 170 (as opposed to that shown in FIG. 13), movement of counterpart 172 towards element 170 would increase the magnetic attractive force between the two components and necessarily cause the movement of element 170 in the direction indicated by arrow B. As discussed above, this lengthens filament 152, while at the same time decreasing its diameter. Thus, this would constitute one alternate design. Similarly, it is possible to provide a single magnetic component with a corresponding metallic component, rather than the above discussed two magnet configuration. Clearly, as is well understood, such components would be attracted to one another. Therefore, operation of this magnet/metal configuration would operate in a like manner to the above discussed opposite polarity magnetic configuration. However, it is to be understood that various configurations are envisioned depending upon the polarity of the magnetic components and/or the situation of the metallic element and its corresponding magnetic element. For example, filament 152 may be wrapped around a metallic element, with a magnetic component located in housing 174 or vice versa.

Figure 15:
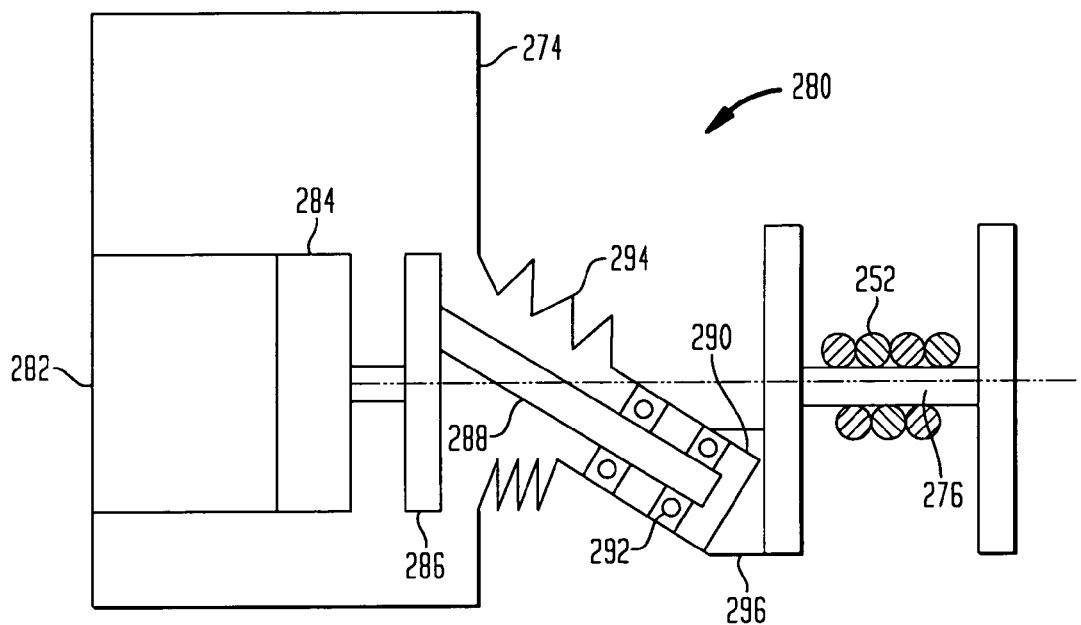
FIG. 15 is a cross sectional view of the driving assembly for use with the flow resistor of FIG. 14.

A fourth example of the first embodiment of the present invention is shown in FIG. 14. This example includes an elastic filament 252 that is fixed at one end by attachment 260 and wrapped around axle 276 on the other. Once again, fluid enters capillary 254 at entrance 266, and exits at exit 268. Fluid flow direction is once again indicated by arrow F. Rotation of axle 276, in a direction depicted by arrow W (i.e.— counter-clockwise), causes filament 252 to lengthen, while its diameter reduces. This, in turn, increases the possible flow rate through capillary 254. Alternatively, rotation of axle 276 in a clockwise direction causes the opposite effect. As previously mentioned, if filament 252 and filament 254 have circular cross sections, the above equations may be utilized in calculating the hydraulic resistance of the system. Axle 276 may be driven directly by a micro motor, via a reduction gear drive assembly 280 as shown in FIG. 15.

While other means may be utilized for driving axle 276, the following sets forth a discussion of the aforementioned reduction gear drive assembly 280. As shown in FIG. 15, assembly 280 presents a solution for the transfer of rotational motion from hermetic enclosure 274 to axle 276. Assembly 280 includes a motor 282 that is augmented by a gear drive 284 and transferred to disc 286. The disc includes a shaft 288 which is preferably positioned at an angle which is less than ninety degree relative to the plane of disc 286. Shaft 288 extends into cylindrical portion 290 of hermetic enclosure 274. Further, shaft 288 is supported via bearings 292 within cylindrical portion 290. Finally, cylindrical portion 290 is connected to enclosure 274 by an elastic connection 294 and is capable of transmitting forces via pusher plate 296 to rotate axle 276. Essentially, the offset nature of the connections between disc 286 and shaft 288, and portion 290 and plate 296, coupled with the elastic nature of the connection between enclosure 274 and portion 290 allows for the rotation of axle 276. It is noted that operation of the motor in different directions causes the rotation of the axle in the clockwise or counter-clockwise direction.

Gear drive assembly 280 is useful for allowing a relatively small or weak motor to drive axle 276. Providing a gear assembly to better utilize a motor is well known. However, any known gear assembly, suitable for use with the present invention, may be employed. Further, it is also contemplated that a suitable motor may be employed that may be capable of directly rotating axle 276. Essentially, in a design like this, axle 276 may be a continuation of the drive shaft of the motor.

Any of the examples set forth in the discussion relating to this first embodiment may include different, additional or fewer elements. Such revisions will be understood by those of ordinary skill in the art. For example, it is envisioned that the various elastic filaments, while shown in the figures having a substantially circular cross section, may include any shaped cross section. Similarly, although shown as substantially straight, the above may be utilized in conjunction with curved capillaries. Additionally, it is to be understood that the inventions set forth in the first embodiment may be utilized with any known implantable pump. The particular pump design may require the use of a resistor that is particularly configured and dimensioned to operate with the pump. Such design requirements are evident to those of ordinary skill in the art.

Figure 16:
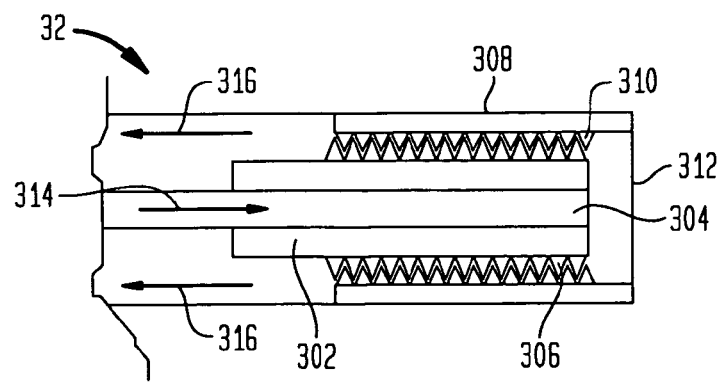
FIG. 16 is a cross sectional view of a variable flow resistor in accordance with a second embodiment of the present invention in a high resistance position.
Figure 17:
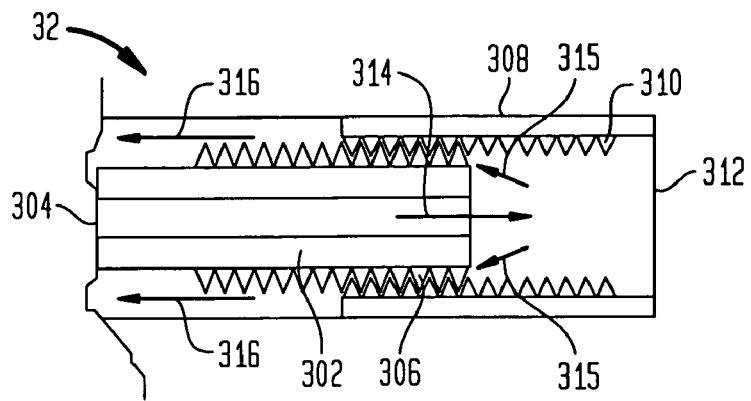
FIG. 17 is a cross sectional view of the variable flow resistor of FIG. 16 in a low resistance position.

In a second embodiment the adjustment of flow rate is realized by providing a pair of threaded matched cylinders for use as resistor 32. Once again, the second embodiment will be discussed with respect to pump 20; however, it may be utilized in combination with any implantable pump. As shown in FIGS. 16 and 17, in accordance with this second embodiment, resistor 32 includes a first threaded member 302 having a hollow interior 304 and a threaded exterior 306. First threaded member is disposed in second threaded member 308, which is an oppositely configured hollow member having a threaded interior surface 310 and a closed end 312. The threaded cooperation between first and second threaded members 302 and 308 allows for the first member to be disposed within the second member at varying levels, therefore, allowing for different overlaps of the two members. For example, FIG. 16 depicts the first member being substantially disposed within the second member, while FIG. 17 depicts the first member being only partially disposed within the second member.

In operation of this second embodiment, fluid is introduced into hollow interior 304 in the direction indicated by arrow 314. Upon the sufficient build up of pressure created by the flow of the fluid, the closed end 312 design of second member 308 forces the fluid to move in the direction indicated by arrow 315 (best shown in FIG. 17) and through the flow channel defined by the threaded configuration of the two members 320, 308. The degree of overlap of the two threaded geometries determines the hydraulic resistance, and thus the flow rate of the fluid. Therefore, the high overlap shown in FIG. 16 would result in a lesser flow rate than that of the low overlap depicted in FIG. 17. Nevertheless, the fluid ultimately emerges from the resistor design as illustrated by arrows 316. It is envisioned that in other examples in accordance with this embodiment of the present invention the shapes of the two members may vary, as can the particular thread design employed.

Figure 18:
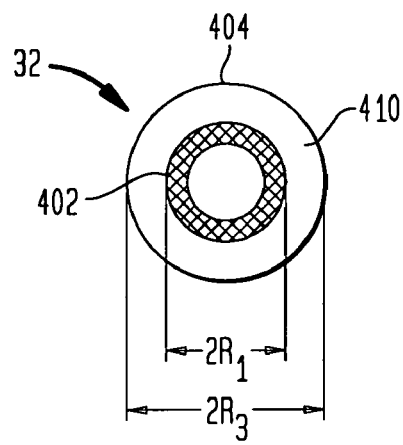
FIG. 18 is a cross sectional view of a variable flow resistor in accordance with a third embodiment of the present invention with an insert centrally located.
Figure 19:
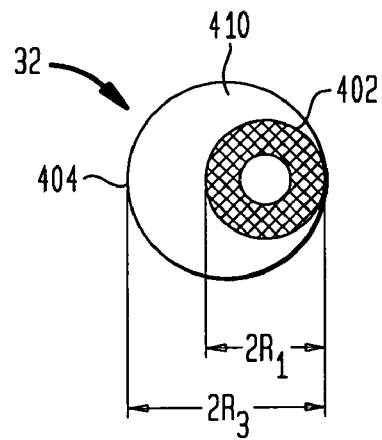
FIG. 19 is a cross sectional view of a variable flow resistor in accordance with a third embodiment of the present invention with an insert eccentrically located.
Figure 20:
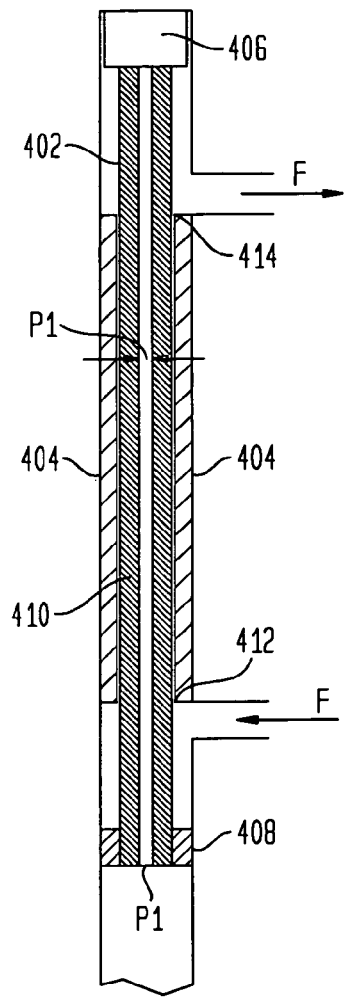
FIG. 20 is a longitudinal cross sectional view of the variable flow resistor of FIG. 18.

In a third embodiment the adjustment of flow rate is realized by adjusting the cross-sectional geometry of the resistor. However, unlike the above discussed first embodiment where the cross-sectional geometry is adjusted by lengthening filament 52 in order to decrease its diameter, this third embodiment varies the cross-sectional geometry of a tube 402 by changing its internal pressure. Once again, the third embodiment will be discussed with respect to pump 20; however, it may be utilized in combination with any implantable pump. As shown in FIGS. 18-20, in accordance with this third embodiment, resistor 32 includes an elastic tubular element 402 disposed in a capillary 404. As best shown in FIG. 20, the tubular element 402 extends through capillary 404 and is fixed at its ends by sealing elements 406 and 408. As shown in FIGS. 18 and 20, the tubular element 402 is situated so as to define a ring-shaped flow channel 410 through capillary 404. However, like the above discussed first embodiment, the tube may be positioned eccentrically, thereby forming a sickle-shaped flow channel 410, as shown in FIG. 19.

In operation, fluid flows in the direction indicated by arrows F, and is subjected to the flow channel from entrance 412 to exit 414. Once again, the effective length of the resistor extends along the portion where tube 402 and capillary 404 overlap. The diameter of tubular element 402 depends upon its internal pressure P1. Thus, the flow rate of the fluid can be affected by pressure being applied or reduced to the inside of tube 402. Rising the pressure will increase the outer diameter of the tubing and thus will have the effect of reducing the flow rate. Similarly, lowering the pressure will decrease the outer diameter of the tubing and increase the flow rate. It is noted that tubular element 402 will have a particular resting diameter (i.e.—with no pressure being applied). The design of this third embodiment will be subject to the flow rate calculations discussed above in relation to the first embodiment. Specifically, in the design shown in FIG. 19, adjusting the tubing between approximately eighty five percent (85%) to ninety percent (90%) of the overall inner diameter of capillary 404 will result in an approximate flow rate variation of 1 to 25, which is the desired ratio for an implantable pump. However, it is to be understood that the operation of this third embodiment will be substantially opposite to that of the first embodiment. Clearly, rather than decreasing the diameter of tube 402 from its resting diameter, this third embodiment aims to increase the diameter. Thus, operation of tube 402 will move the system from a state in which the flow rate is greater to a state where the flow rate is lesser. This is contrary to the first embodiment.

Any means suitable for rising and lowering the pressure to the inside of tubular element 402 can be utilized. For example, it is envisioned that a piston or bellows assembly may be utilized, or that a chemical reaction may be employed to achieve the pressure differential.

Figure 21:
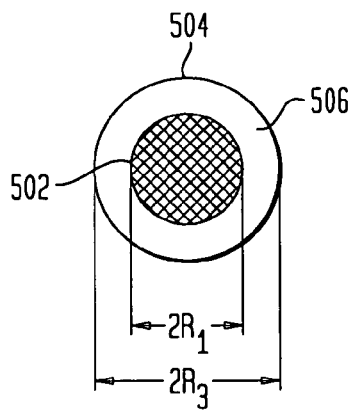
FIG. 21 is a cross sectional view of the larger end of a variable flow resistor in accordance with a fourth embodiment of the present invention with an insert centrally located.
Figure 22:
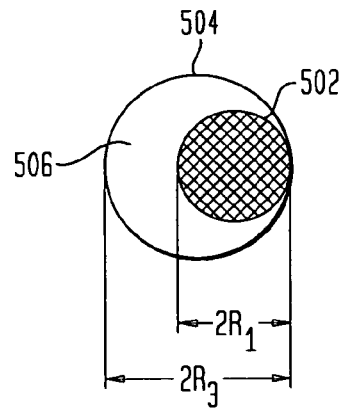
FIG. 22 is a cross sectional view of the larger end of a variable flow resistor in accordance with a fourth embodiment of the present invention with an insert eccentrically located.
Figure 23:
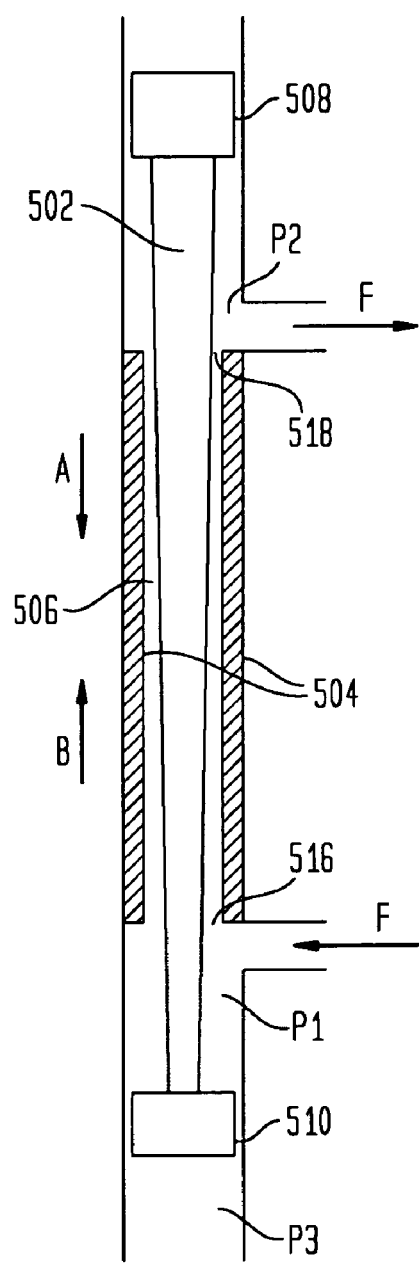
FIG. 23 is a longitudinal cross sectional view of the variable flow resistor of FIG. 21.
Figure 24:
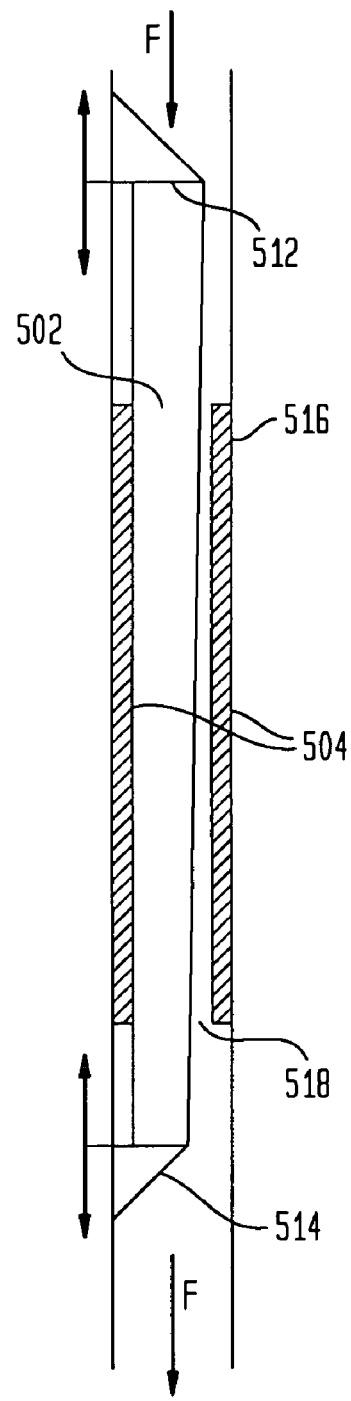
FIG. 24 is a longitudinal cross sectional view of the variable flow resistor of FIG. 22.

In a fourth embodiment the adjustment of flow rate is realized by providing an insert 502 having a longitudinally varying cross section. By moving the insert 502 along the longitudinal axis of a capillary 504, the hydraulic resistance of resistor 32 is changed. Once again, the fourth embodiment will be discussed with respect to pump 20; however, it may be utilized in combination with any implantable pump. As shown in FIGS. 21-24, in accordance with this fourth embodiment, resistor 32 includes the aforementioned insert 502 positioned within a capillary 504. In one example of this fourth embodiment, as is shown in FIGS. 21 and 23, insert 502 is depicted as having a conical shape, and is centrally located within capillary 504. Thus, the cross section of insert 502 varies across its longitudinal axis and the design forms a ring-shaped flow channel 506. This insert is fixed at its ends to two movable piston-like attachments 508, 510. However, another example is shown in FIGS. 23 and 24, in which insert 502 may be positioned eccentrically resulting in a sickle-shaped flow channel 506. In this example, insert 502 is fixed at its ends to two movable fixations 512, 514.

In operation of both examples, fluid flows in the direction indicated by arrows F, and is subjected to the flow channel from entrance 516 to exit 518 (i.e.—the aforementioned effective length). While the above-discussed equations relating to the flow rate do not necessarily apply to this embodiment, it is clear that the width of flow channel 506 may be varied by moving insert 502 in the direction of the axis of capillary 504. For example, as shown in FIG. 23, movement of insert 502 in the direction depicted by arrow A will cause a decrease in the width of flow channel 506, and thus a decrease in the flow rate of the fluid. Alternatively, movement of insert 502 in the direction depicted by arrow B will cause an increase in the width of flow channel 506, and thus an increase in the flow rate of the fluid.

It is noted that the movement of insert 502 may be achieved in different fashions depending upon the type of design utilized. For example, as shown in FIG. 23, piston-like attachments 508, 510 are preferably moved by providing a suitable pressure thereto. However, as shown in FIG. 24, movable fixations 512, 514 may also be utilized that are moved by providing a mechanical force thereto, from source such as a hydraulic, electrical or mechanical source or the like. Various means may be employed for providing movement to insert 502, including those discussed herein and others that would be well known to those skilled in the art. For example, once again, magnetic forces may be employed for moving insert 502. Finally, insert 502 may include a varying cross section that creates a substantially smooth longitudinal surface, as shown in the figures, or, insert 502 may be comprised of several non-congruent cross sectional portions. The latter configuration would provide an insert that has several different stepped sections. Thus, moving a first section into capillary 504 having a relatively large cross section would most likely reduce the flow rate, while moving a second section of lesser cross section would increase the flow rate.

The various embodiments of resistor 32, in accordance with the present invention, should be positioned such that fluid housed in the slow release chamber of an implantable pump is forced to pass through it. This configuration allows for the implantable pump to operate in its normal fashion, with resistor 32 controlling the fluid flow rate. However, preferred constructions would situate resistor 32 such that an injection into a bolus port or the like would not be forced to pass through the resistor. It is typically not required to control the flow rate of a bolus injection. Rather, such an injection is often intended to be a quick and direct application of a medication fluid. For example, as shown in FIG. 7, resistor 32 is situated so as to capture fluid flowing from chamber 24, but not fluid directly injected into bolus port 46. However, other constructions are envisioned. Furthermore, where the implantable pump is utilized to withdraw spinal fluid, it is also contemplated to not force such fluid through resistor 32. In the pump of FIG. 7, withdrawal of spinal fluid would occur through bolus port 46. As such, the fluid would not be required to pass through the resistor.

For each of the embodiments above, providing a controlling mechanism for selectively varying the flow rate of the medication fluid is envisioned. Many different such mechanisms are well known and widely utilized with implantable devices for implantation into a patient's body. For example, prior art devices have shown that it is possible to utilize dedicated hard wired controllers, infrared controllers, or the like, which controllers could be used in accordance with the present invention to control various elements, such as motor 282, to selectively vary the flow rate of the medication fluid. U.S. Pat. No. 6,589,205 ("the '205 patent"), the disclosure of which is hereby incorporated by reference herein, teaches the use of a wireless external control. As discussed in the '205 patent, such a wireless control signal may be provided through modulation of an RF power signal that is inductively linked with the pump. The '205 cites and incorporates by reference U.S. Pat. No. 5,876,425, the disclosure of which is also hereby incorporated by reference herein, to teach one such use of forward telemetry or the exchange of information and programming instructions that can be used with the present invention to control the pump and the various aforementioned elements that are varied in order to affect the flow rate. However, it is noted that similar external controllers may also be utilized. Such controllers can send control signals wirelessly (such as by IR, RF or other frequencies) or can be wired to leads that are near or on the surface of the patient's skin for sending control signals. Furthermore, a pump in accordance with the present invention may include safeguards to prevent the inadvertent signaling or improper programming of the pump. For example, the present invention could utilize a secure preamble code or encrypted signals that will be checked by software or hardware used for controlling the pump or even dedicated only for security purposes. This preamble code would prevent the inadvertent varying of the flow rate of the fluid from the pump, from being caused by outside unrelated remote control devices or signals and by other similar pump controllers. Other safety precautions may be used, such as passwords, hardware or software keys, encryption, multiple confirmation requests or sequences, etc. by the software or hardware used in the programming of the pump.

The electronics and control logic that can be used with the present invention for control of the motors and controllably displaceable elements used to vary the flow rate may include microprocessors, microcontrollers, integrated circuits, transducers, etc. that may be located internally with or in the implantable pump and/or externally with any external programmer device to transmit pump programming information to control the pump. For example, any external programmer device used to allowing programming of the pump. The electronics can also be used to perform various tests, checks of status, and even store information about the operation of the pump or other physiological information sensed by various transducers.

An external programmer device may also be avoided by incorporating the necessary logic and electronics in or near or in the implantable pump such that control can be accomplished, for example, via control buttons or switches or the like that can be disposed on or below the surface of the skin. Of course, necessary precautions (such as confirmation button pressing routines) would need to be taken so that inadvertent changing of programming is again avoided.

A specific implantable pump 700, which incorporates the above discussed reduced size designs, as well as the above discussed infinitely variable designs of the present invention will now be described. Essentially, pump 700 is an implantable pump having certain novel characteristics. These characteristics allow for both the relative miniaturization and easy construction of the pump. In addition, pump 700 incorporates one of the aforementioned resistor 32 designs into the specific embodiment. While pump 700 is indeed one preferred embodiment for use in accordance with the present invention, it should be clearly understood that the pump could be modified to incorporate each of the resistor 32 designs discussed above in many different configurations.

Figure 25:
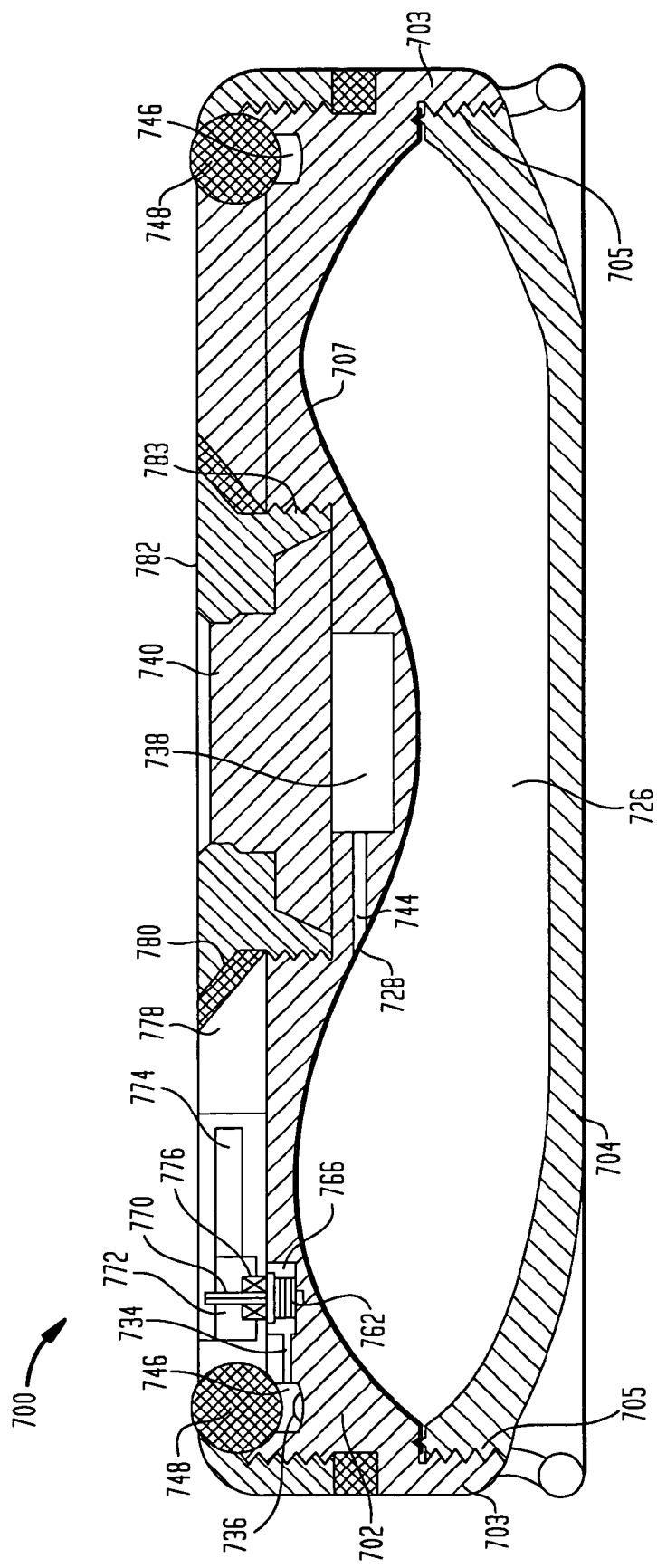
FIG. 25 is a cross sectional view of an implantable pump in accordance with another embodiment of the present invention.
Figure 26:
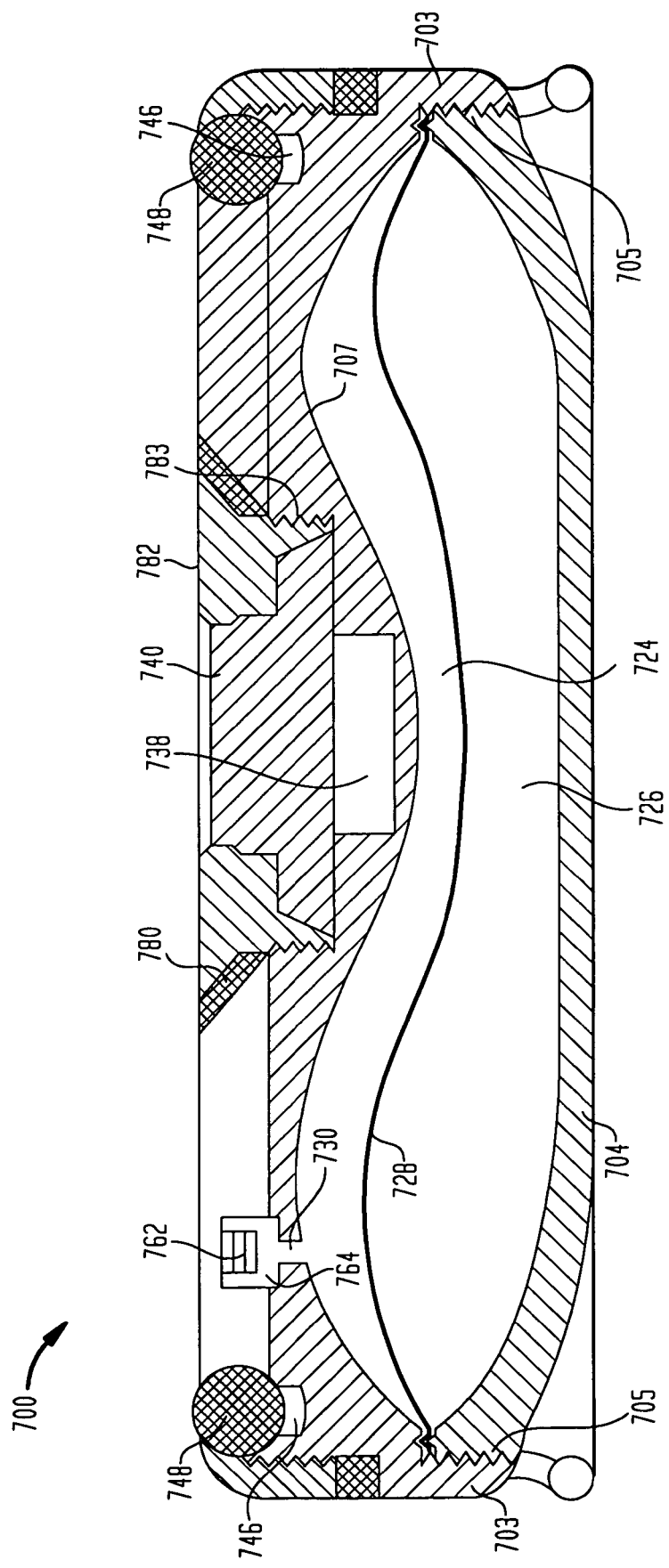
FIG. 26 is a cross sectional view of the implantable pump shown in FIG. 25, taken along a different portion thereof.

As shown in FIGS. 25 and 26, pump 700 includes a housing constructed of an upper portion 702 and a lower portion 704. The housing portions are preferably constructed of a strong polymeric material, such as polyetheretherketone, sold under the designation PEEK by Invibio of the United Kingdom. Other suitable materials may also be employed. Nevertheless, the particular material should be chosen so as to be capable of forming a two part housing that can be safely assembled without the use of a complicated double clinch assembly, a welding process or the like. Clearly, safety is a very big concern in the construction of any apparatus inserted into the body especially one housing an overdose of medication solution. Heretofore, implantable pump housings have either been constructed of a metallic material, wherein a welding process is utilized for attaching the portions of the housing together, or a polymeric material, wherein a complicated clinching assembly is utilized for attaching the portions of the housing together. For example, a metallic pump is typically constructed by welding together two metallic halves of the pump housing. Similarly, as taught in commonly owned U.S. Pat. Nos. 5,814,019 and 5,836,915, a double clinching assembly has been previously proposed for safely attaching the housing halves of a polymeric pump.

In accordance with the present invention, it has been discovered that utilizing a material such as PEEK may allow for a polymeric pump housing to be constructed without the use of any of the complicated attachment procedures. The elimination of such extraneous elements allows for pump 700 to be smaller in size. For example, the elimination of the aforementioned double clinch safety feature allows for the overall width of pump 700 to be reduced. Further, in certain embodiments, this may also decrease the overall weight of the pump, as well as the level of complicity required in assembling same. As shown in FIG. 25, portions 702 and 704 of the housing of pump 700 are constructed of PEEK and designed so as to be capable of simply screwing together. More particularly, portion 702 includes an interiorly threaded extension 703 for receiving an exteriorly threaded surface 705 of portion 704. In certain embodiments, in addition to the threaded connection, a layer of glue or other adhesive may be applied to the connection between portions 702 and 704. Such an application may provide further assurance that the two portions do not inadvertently become detached. It is also contemplated that other less complicated attachment modes may be employed. For example, in addition to the threadable connection between portions 702 and 704, a single clinch connection may be utilized. In this type of attachment, the two portions may include elements that are designed so as to snap fit together, and thereafter fixably secure the portions together.

As with the aforementioned generic pump 20 design, implantable pump 700 further includes an interior having two chambers 724 and 726, each chamber being separated by a flexible membrane 728. Chamber 724 is designed to receive and house an active substance such as a medication fluid, while chamber 726 is designed to house a propellant that expands isobarically under constant body temperature. Similar to above discussed generic pump 20, the expansion of the propellant in pump 700 displaces membrane 728 such that the medication fluid housed in chamber 724 is dispensed into the body of the patient through the path defined by an outlet opening 730 (FIG. 26), a cylindrical recess 764, a resistor 732 (FIG. 27), a cylindrical recess 766 (FIG. 25), an outlet duct 734 and ultimately an outlet catheter 736. Also in accordance with pump 20, pump 700 further includes a replenishment port 738 covered by a first septum 740, and an annular ring bolus port 746 covered by a second ring shaped septum 748. The utility of each of these ports is substantially identical to those of pump 20. For example, a passage 744 allows fluid injected into replenishment port 738 to be introduced into chamber 724. In addition, like that of pump 20, it is envisioned that specifically designed injection needles and correspondingly situated septa may be employed to increase safety, as discussed above.

Contrary to the aforementioned pump 20, pump 700 includes an undulating membrane 728 which cooperates with a similarly undulating interior surface 707 of portion 702. As best shown in FIGS. 25 and 26, interior surface 707 of portion 702 has an undulating surface that serves as the top surface of chamber 724, while membrane 724 has a corresponding undulating surface that serves as the bottom surface of chamber 724. When chamber 724 is empty, membrane 724 fits flush against the similarly shaped interior surface 707. This is best shown in FIG. 25. However, upon introduction of a fluid into chamber 724, membrane 728 is capable of flexing and allowing for the expansion of chamber 724. This is best shown in FIG. 26. This undulating configuration of membrane 728 and interior surface 707 of portion 702 allows for replenishment port 738 and septum 740 to be situated at a lower position with respect to the height of the pump. Essentially, a center portion of both interior surface 707 and membrane 728 are a convex shape allowing for portion 738 and septum 740 to be set lower. At the same time, portions to the left and right of this center portion are enlarged, taking substantially concave shapes. This allows for the overall volume of chamber 724 to remain substantially similar in comparison to well-known implantable pumps. Operation of pump 700 also remains substantially similar to prior art implantable pumps being driven by a propellant. While the specific undulating design (i.e.—a convex or lower portion flanked by two concave or higher portions), shown in FIGS. 25 and 26, is one suitable embodiment, other embodiments are envisioned. For example, other pumps may include surfaces and membranes that have corresponding shapes having multiple concave and/ or convex portions.

Figure 27:
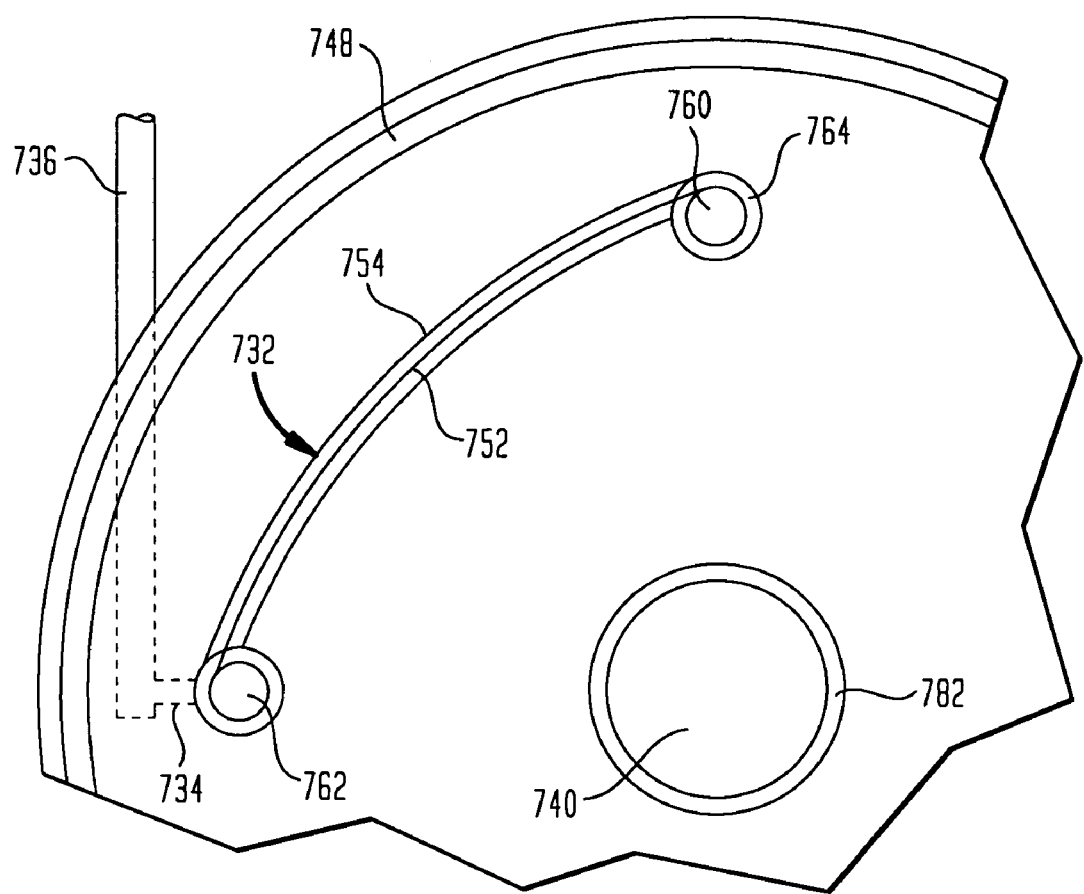
FIG. 27 is a partial top view of the implantable pump shown in FIG. 25.

The specific construction and cooperation of resistor 732 within pump 700 is shown in detail in FIGS. 25-27. The resistor shown in this specific embodiment is akin to the above described first embodiment resistor. As best shown in FIG. 27, resistor 732 includes an elastic and resilient filament 752 situated in a capillary 754. Filament 752 extends through capillary 754 and is attached on its ends to two spools 760 and 762. Spool 760 resides within cylindrical recess 764 in fluid communication with opening 730 in portion 702, while spool 762 resides within a cylindrical recess 766 in portion 702. Recess 764 is in fluid communication with outlet opening 730 and hence chamber 724 (best shown in FIG. 26). Similarly, recess 766 is in fluid communication with outlet duct 734, and hence outlet catheter 736 (best shown in FIG. 25). Thus, fluid will flow from chamber 724 through resistor 732, and out of catheter 736 to a target site within the body.

As best shown in FIG. 27, capillary 754 is preferably curved so as to force filament 752 to one side thereof. Spools 760 and 762 are adapted to wind filament 752 thereon and thus vary its cross section. As more specifically discussed above, this varying in cross section varies the flow rate of fluid through capillary 754. In the embodiment shown in FIGS. 25-27, spool 760 is adapted to remain in a fixed position, while spool 762 is adapted to be rotated. However, in other embodiments, both spools may be adapted to be rotated. As best shown in the cross sectional view of FIG. 25, spool 762 is mechanically coupled to several actuation components including being coupled via an axle 770 to a wheel 772. A motor 774, like that of the above mentioned X15G, is employed to provide rotation to wheel 772. A bearing 776 or the like may aid in the rotation of axle 770, by guiding and providing smooth motion to axle 770. In the embodiment shown in the figure, motor 774 receives electrical energy and control from an electronic unit 778, which, as discussed above, controlled from either internally or externally of the body.

The aforementioned actuation components are held together and within pump 700 through a specific cooperation that is best shown in FIG. 25. Essentially, ring septum 748 and an elastic element 780 are designed to hold the actuation components to pump 700. The actuation elements are preferably housed so as to be a single module encompassing spool 762, axle 770, wheel 772, motor 774, bearing 776 and electronic unit 778. During assembly, this module is placed into a recess on pump 700 so that one side abuts ring septum 748. With the module in place, septum 740 is attached to portion 702 by screwing a holder 782, which holds septum 740, to portion 702 of pump 700, so as to form a threaded connection 783. Holder 782 is preferably constructed of PEEK material like portions 702 and 704. It is also contemplated that other modes of attachment may be employed, such as, by adhesive or a combination of adhesive and threads. Ring 780 of elastomeric material is preferably placed between holder 782 and electronic unit 778, and the cooperation thereof holds the aforementioned module between septum 748 and ring 780. Essentially, one side of the module is designed to cooperate with septum 748 (i.e.—curved cooperation), while the other side is designed to cooperate with ring 780 (i.e.—sloped cooperation). Thus, in the fully constructed state, the module of actuation components is essentially frictonally attached to pump 700.

The specific embodiment shown in FIGS. 25-27 also allows for an easy conversion from a variable flow rate pump to a fixed flow rate pump. In operation, the manufacturer or user of the pump would simply remove the aforementioned module of actuation components. A spacer, insert or the like may inserted into any cavity formed in the housing of pump 700, after the removal of the module. Filament 752 is also removed from capillary 754 and replaced with a small tube (not shown), constructed of a material such as glass. The tube preferably has an outer diameter slightly smaller than the inside diameter of capillary 754, so as to allow a snug fit therein. Further, the tube may have any suitable inner diameter, it being noted that the particular inner diameter size dictates the flow rate of fluid through capillary 754. Thus, depending upon the desired fixed flow rate, a particular tube having a suitable inner diameter should be selected. Finally, the tube should be capable of conforming to the preferable curved shape of capillary 754. With these simple modifications to pump 700, a relatively inexpensive fixed flow rate pump may be produced. This simple conversion allows for the use of the majority of the components of pump 700 without requiring the modification of any. This is beneficial, because new molds or the like would not be needed to change between pump designs.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An implantable device for dispensing an active substance to a patient comprising:
   a housing having top and bottom portions defining an active substance chamber in fluid communication with an outlet for delivering said active substance to a target site within said patient, and a propellant chamber adjacent said active substance chamber, the top portion including a replenishment opening; and,
   an undulating flexible membrane separating said active substance and propellant chambers, said undulating flexible membrane having a first position when said active substance chamber is empty and a second position when said active substance chamber contains an active substance,
   wherein said top portion has an undulating interior surface including a continuously curved central convex portion flanked by at least two continuously curved concave portions and said undulating flexible membrane has a continuously curved central concave portion flanked by at least two continuously curved convex portions in both the first and second positions, said undulating interior surface cooperating with said undulating flexible membrane in the first position, and wherein said replenishment opening is located within said central convex portion of said undulating interior surface so as to lower an overall height of said implantable device,
   wherein said undulating interior surface of said top portion and said concave and convex portions of said undulating flexible membrane include no flat portions.

2. The implantable device according to claim 1, wherein the propellant chamber contains a propellant capable of expanding isobarically, the propellant cooperating with said undulating flexible membrane to reduce the volume of the active substance chamber upon expansion of the propellant.

3. The implantable device according to claim 2, wherein the cooperating undulating surface and said undulating flexible membrane meet upon complete expansion of the propellant.

4. The implantable device according to claim 1, further comprising a first septum sealing said replenishment opening.

5. The implantable device according to claim 4, further comprising an annular opening in said housing communicating with said outlet, and a second septum sealing the annular opening.

6. The implantable device according to claim 1, further comprising means for varying the flow rate of said active substance between said active substance chamber and said outlet.

7. The implantable device according to claim 6, wherein said means includes an elongated polymer filament having a cross sectional dimension, the filament capable of being elongated to reduce the cross sectional dimension.

8. The implantable device according to claim 7, further including a capillary in fluid communication between said chamber and said outlet, wherein the filament is located eccentrically within said capillary.

9. The implantable device according to claim 8, wherein the filament has a uniform cross section along its length.

10. The implantable device according to claim 8, wherein the filament has a non-uniform cross section along its length.

11. The implantable device according to claim 7, further comprising means for elongating the filament.

12. The implantable device according to claim 11, wherein said means for elongating the filament includes an axle driven by a motor.

13. The implantable device according to claim 6, further comprising means for controlling said means for varying the flow rate of said active substance between said chamber and said outlet.

14. The implantable device according to claim 13, wherein the means for controlling are wireless.

15. The implantable device according to claim 1, further comprising a capillary in fluid communication between said active substance chamber and said outlet, said capillary having an inner surface, and a flow control element received within said capillary, said element having an outer surface opposing said inner surface of said capillary defining therebetween a passageway for the flow of said active substance therethrough, said outer surface of said element moveable relative to said inner surface of said capillary to alter the flow of said active substance therethrough.

16. The implantable device according to claim 1, wherein said top and bottom portions are constructed so as to screw together.

17. The implantable device according to claim 16, wherein said top and bottom portions of said housing are constructed of polyetherehterketone.

18. The implantable device according to claim 1, wherein said top portion and said bottom portion capture said membrane therebetween.

19. The implantable device according to claim 18, wherein said top portion and said bottom portion form means for retaining said membrane therebetween.

20. The implantable device according to claim 18, wherein said housing further comprises a locking portion which may be screwed into either or both of said top portion or said bottom portion to retain said top portion and said bottom portion together.

21. The implantable device according to claim 20, wherein said housing further comprises a septum retaining member for retaining a replenishment septum covering the replenishment opening.

22. The implantable device according to claim 1, wherein said active substance chamber is defined by said undulating interior surface and said undulating flexible membrane.

23. An implantable device for dispensing an active substance to a patient comprising:
   a housing defining an active substance chamber in fluid communication with an outlet for delivering said active substance to a target site within said patient, and a propellant chamber, said housing having a top portion and a bottom portion, said top portion including a replenishment opening in communication with said chamber and located within a continuously curved central convex portion so as to lower an overall height of said implantable device; and,
   an undulating flexible membrane separating said active substance and propellant chambers, having a first position when said active substance chamber is empty and a second position when said active substance chamber contains an active substance, said undulating flexible membrane including a continuously curved central concave portion in both the first and second positions that cooperates with the central convex portion of said top portion while in the first position,
   wherein the continuously curved central convex portion of said top portion and the continuously curved central concave of said undulating flexible membrane include no flat portions and the first portion and the second portion are constructed of polyetherehterketone and screwed together.

24. The implantable device according to claim 23, wherein the propellant chamber contains a propellant capable of expanding isobarically, the propellant cooperating with said flexible membrane to reduce the volume of the active substance chamber upon expansion of the propellant.

25. The implantable device according to claim 24, wherein said central convex portion and said undulating flexible membrane meet upon complete expansion of the propellant.

26. The implantable device according to claim 25, further comprising a first septum sealing said replenishment opening.

27. The implantable device according to claim 26, further comprising an annular opening in said housing communicating with said outlet, and a second septum sealing the annular opening.

28. The implantable device according to claim 23, further comprising means for varying the flow rate of said active substance between said active substance chamber and said outlet.

29. The implantable device according to claim 28, wherein said means includes an elongated polymer filament having a cross sectional dimension, the filament capable of being elongated to reduce the cross sectional dimension.

30. The implantable device according to claim 29, further including a capillary in fluid communication between said chamber and said outlet, wherein the filament is located eccentrically within said capillary.

31. The implantable device according to claim 30, wherein the filament has a uniform cross section along its length.

32. The implantable device according to claim 30, wherein the filament has a non-uniform cross section along its length.

33. The implantable device according to claim 29, further comprising means for elongating the filament.

34. The implantable device according to claim 33, wherein said means for elongating the filament includes an axle driven by a motor.

35. The implantable device according to claim 28, further comprising means for controlling said means for varying the flow rate of said active substance between said chamber and said outlet.

36. The implantable device according to claim 35, wherein the means for controlling are wireless.

37. The implantable device according to claim 23, further comprising a capillary in fluid communication between said active substance chamber and said outlet, said capillary having an inner surface, and a flow control element received within said capillary, said element having an outer surface opposing said inner surface of said capillary defining therebetween a passageway for the flow of said active substance therethrough, said outer surface of said element moveable relative to said inner surface of said capillary to alter the flow of said active substance therethrough.

38. The implantable device according to claim 23, wherein said active substance chamber is defined by said central convex portion and said undulating flexible membrane.

39. An implantable device for dispensing an active substance comprising:
a housing including a top portion, a bottom portion and a locking portion, said housing defining a propellant chamber and an active substance chamber in fluid communication with an outlet, said top portion including a replenishment opening located within a continuously curved convex portion so as to lower an overall height of said implantable device; and
a membrane retained between said top and bottom portions having a first position when said active substance chamber is empty and a second position when said active substance chamber contains an active substance, said membrane separating said active substance and propellant chambers and including a continuously curved concave portion in both the first and second positions that cooperates with the continuously curved convex portion of said top portion while in the first position,
wherein the continuously curved convex portion of said top portion and the continuously curved concave portion of said membrane include no flat portions and said top and bottom portions are placed together and said locking portion is screwed into either or both of said top or bottom portions to retain said top and bottom portions together.

40. The implantable device according to claim 39, wherein said top and bottom portions form an attachment for retaining said membrane therebetween.

41. The implantable device according to claim 39, wherein the propellant chamber contains a propellant capable of expanding isobarically, the propellant cooperating with said flexible membrane to reduce the volume of the active substance chamber upon expansion of the propellant.

42. The implantable device according to claim 39, wherein said top portion further includes at least two continuously curved concave portions flanking said central convex portion.

43. The implantable device according to claim 42, further comprising a first septum sealing said replenishment opening.

44. The implantable device according to claim 43, further comprising an annular opening in said housing communicating with said outlet, and a second septum sealing the annular opening.

45. The implantable device according to claim 44, wherein said housing further comprises a septum retaining member for retaining said first septum.

46. The implantable device according to claim 42, wherein said active substance chamber is defined by said concave and convex portions and said membrane.

47. The implantable device according to claim 39, wherein said top, bottom and locking portions are constructed from polyetherehterketone.

* * * * *